(12) United States Patent
Hamm et al.

(10) Patent No.: US 8,076,139 B1
(45) Date of Patent: Dec. 13, 2011

(54) PROCESSES AND COMPOSITIONS FOR TRANSFECTING CHINESE HAMSTER OVARY (CHO) CELLS

(75) Inventors: Sarah E. Hamm, St. Louis, MO (US); William P. Leinert, Wildwood, MO (US)

(73) Assignee: Leinco Technologies, Inc., St. Louis, MO (US)

( * ) Notice: Subject to any disclaimer, the term of this patent is extended or adjusted under 35 U.S.C. 154(b) by 547 days.

(21) Appl. No.: 11/750,401

(22) Filed: May 18, 2007

Related U.S. Application Data

(60) Provisional application No. 60/846,664, filed on Sep. 22, 2006, provisional application No. 60/843,186, filed on Sep. 8, 2006, provisional application No. 60/802,914, filed on May 24, 2006, provisional application No. 60/802,041, filed on May 19, 2006.

(51) Int. Cl.
*C12N 15/00* (2006.01)
*C12N 15/85* (2006.01)
*C12N 15/88* (2006.01)

(52) U.S. Cl. ............... 435/455; 435/320.1; 435/325; 424/484; 424/486

(58) Field of Classification Search .......... 435/455, 435/320.1, 325, 69.1; 424/450, 484, 486
See application file for complete search history.

(56) References Cited

U.S. PATENT DOCUMENTS

| | | | |
|---|---|---|---|
| 5,024,939 A | 6/1991 | Gorman | |
| 2005/0170450 A1 | 8/2005 | Durocher et al. | |

OTHER PUBLICATIONS

Dunlap DD et al., Nanoscopic structure of DNA condensed for gene deliveryNucleic Acids Res. Aug. 1, 1997;25(15):3095-101.*
Godbey et al., Poly(ethylenimine) and its role in gene deliveryJournal of Controlled Release vol. 60, Issues 2-3, Aug. 5, 1999, pp. 149-160.*
Behr, J-P., "Gene Transfer with Synthetic Cationic Amphiphiles: Prospects for Gene Therapy," Bioconjugate Chem., 1994, pp. 382-389, vol. 5, No. 5.
Boussif, O., et al., "A Versatile Vector for Gene and Oligonucleotide Transfer into Cells in Culture and in vivo: Polyethylenimine," Proc. Natl. Acad. Sci. USA, Aug. 1995, pp. 7297-7301, vol. 92.
Cheryan, Ph.D., M., Ultrafiltration Handbook, Chapter 1, 1986, pp. 1-26, Technomic Pub. Co.
Cotten, M., et al., "Non-Viral Approaches to Gene Therapy," Current Opinion in Biotechnology, 1993, pp. 705-710, vol. 4.
D'Anna, J. A., et al., "Association of G1/S-Phase and Late S-Phase Checkpoints with Regulation of Cyclin-Dependent Kinases in Chinese Hamster Ovary Cells," Radiation Research, 1997, pp. 260-271, vol. 148.
D'Anna, J. A., et al., "Synchronization of Mammalian Cells in S Phase by Sequential Use of Isoleucine-Deprivation G1- or Serum-Withdrawal Go-Arrest and Aphidicolin Block," Methods in Cell Science, Jun. 1996, pp. 115-125, vol. 18.
Deaven, L. L., et al., "The Chromosomes of CHO, an Aneuploid Chinese Hamster Cell Line: G-Band, C-Band, and Autoradiographic Analyses," Chromosoma, 1973, pp. 192-144, vol. 41.
Derouazi, M., et al., "Serum-Free Large-Scale Transient Transfection of CHO Cells," Biotechnology and Bioengineering, Aug. 20, 2004, pp. 537-545, vol. 87, No. 4.
Dobyrnin, A. V., et al., "Theory of Polydisperse Multiblock Copolymers," Macromolecules, 1997, pp. 4756-4765, vol. 30, No. 16.
Durocher, Y., et al., "High-Level and High-Throughout Recombinant Protein Production by Transient Transfection of Suspension-Growing Human 293-EBNA1 Cells," Nucleic Acids Research, 2002, 9 Pages, vol. 30, No. 2 e9.
Frese, Jr., J., et al., "Targeting of Genes to the Liver with Glycoprotein Carriers," Advanced Drug Delivery Reviews, 1994, pp. 137-152, vol. 14.
Haensler, J., et al., "Polyamidoamine Cascade Polymers Mediate Efficient Transfection of Cells in Culture," Bioconjugate Chem., 1993, pp. 372-379, vol. 4, No. 5.
Ham, R. G., "Clonal Growth of Mammalian Cells in a Chemically Defined, Synthetic Medium," Proc. Natl. Acad. Sci. USA, 1965, pp. 288-293, vol. 53.
Hayter, J. B., "Determination of the Structure and Dynamics of Micellar Solutions by Neutron Small-Angle Scattering," Physics of Amphiphiles: Micelles, Vesicles and Microemulsions, 1985, pp. 59-93.
Horbinski, C., et al., "Polyethyleneimine-Mediated Transfection of Cultured Postmitotic Neurons from Rat Sympathetic Ganglia and Adult Human Retina," BMC Neuroscience, 2001, 8 Pages, vol. 2, No. 2.
Kao, F-T., et al., "Genetics of Somatic Mammalian Cells, VII. Induction and Isolation of Nutritional Mutants in Chinese Hamster Cells," Proc. Natl. Acad. Sci. USA, 1968, pp. 1275-1281, vol. 60.
Legendre, J-Y., et al., "Cyclic Amphipathic Peptide-DNA Complexes Mediate High-Efficiency Transfection of Adherent Mammalian Cells," Proc. Natl. Acad. Sci. USA, Feb. 1993, pp. 893-897, vol. 90.
Meissner, P., et al., "Transient Gene Expression: Recombinant Protein Production with Suspension-Adapted HEK293-EBNA Cells," Biotechnology and Bioengineering, Oct. 20, 2001, pp. 197-203, vol. 75, No. 2.
Puck, Ph.D., T. T., et al., "Genetics of Somatic Mammalian Cells," J. Exp. Med., 1958, pp. 945-956, vol. 108.
Schifferli, K. P., et al., "Transfection of Suspension Cultures of CHO Cells," Focus, 1999, pp. 16-17, vol. 21, No. 1.
Sinacore, M. S., et al., "CHO DUKX Cell Lineages Preadapted to Growth in Serum-Free Suspension Culture Enable Rapid Development of Cell Culture Processes for the Manufacture of Recombinant Proteins," Biotechnology and Bioengineering, Nov. 20, 1996, pp. 518-528, vol. 52, No. 4.
Stanley, P., et al., "Selection and Characterization of Eight Phenotypically Distinct Lines of Lectin-Resistant Chinese Hamster Ovary Cells," Cell, Oct. 1975, pp. 121-128, vol. 6.
Urlaub, G., et al., "Isolation of Chinese Hamster Cell Mutants Deficient in Dihydrofolate Reductase Activity," Proc. Natl. Acad. Sci. USA, Jul. 1980, pp. 4216-4220, vol. 77, No. 7.
Wurm, F. M., "Production of Recombinant Protein Therapeutics in Cultivated Mammalian Cells," Nature Biotechnology, Nov. 2004, pp. 1393-1398, vol. 22, No. 11.
Product brochure for Brookhaven 90Plus Nanoparticle Size Analyzer, pp. 1-4 (date unknown; downloaded from http://www.bic.com/90Plus.html?submenuheader=0 on Jul. 29, 2009).

* cited by examiner

*Primary Examiner* — Maria Leavitt
(74) *Attorney, Agent, or Firm* — Bryan Cave LLP

(57) ABSTRACT

The present invention generally relates to processes and compositions for the transfection of Chinese hamster ovary (CHO) cells. More specifically, the present invention relates to processes for the transfection of CHO cells suspended in an aqueous medium using a transfection composition containing nucleic acid and linear polyethyleneimine.

5 Claims, 21 Drawing Sheets

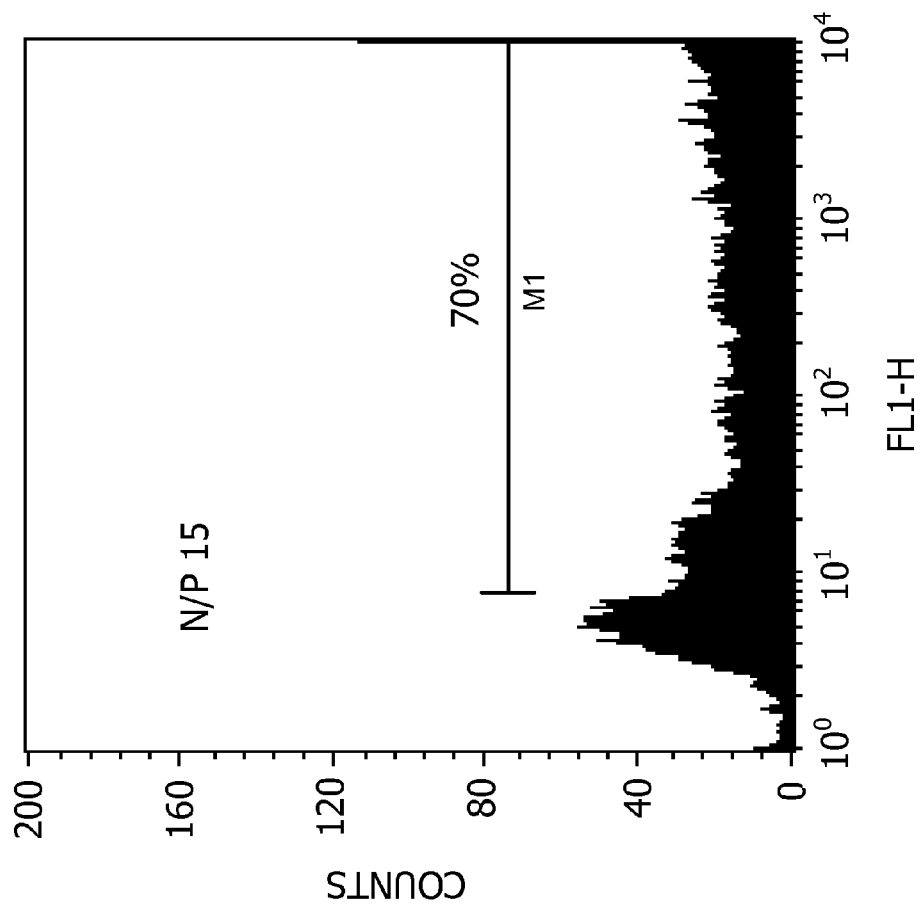

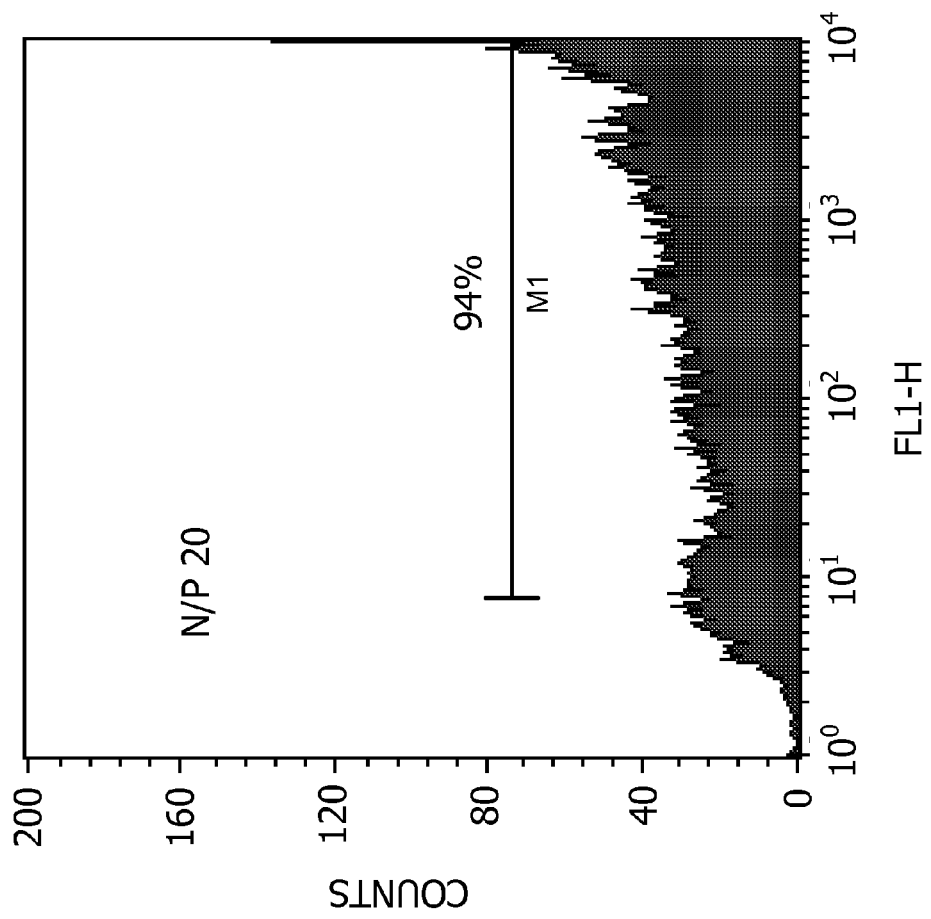

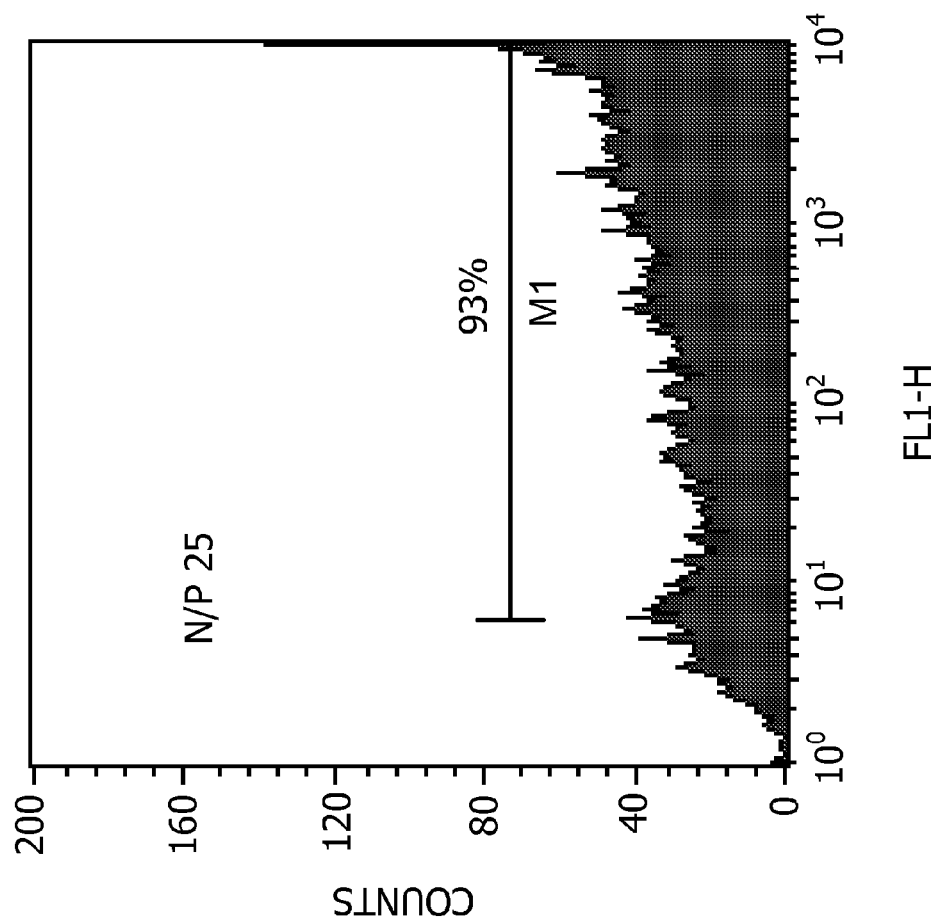

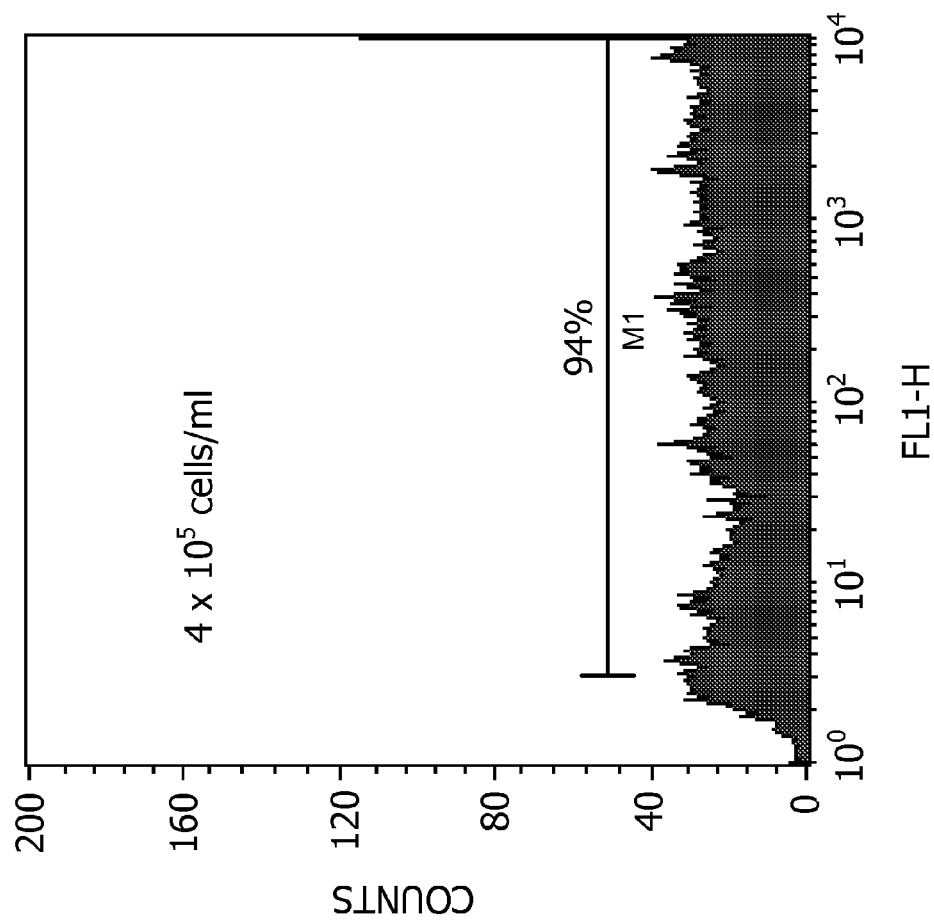

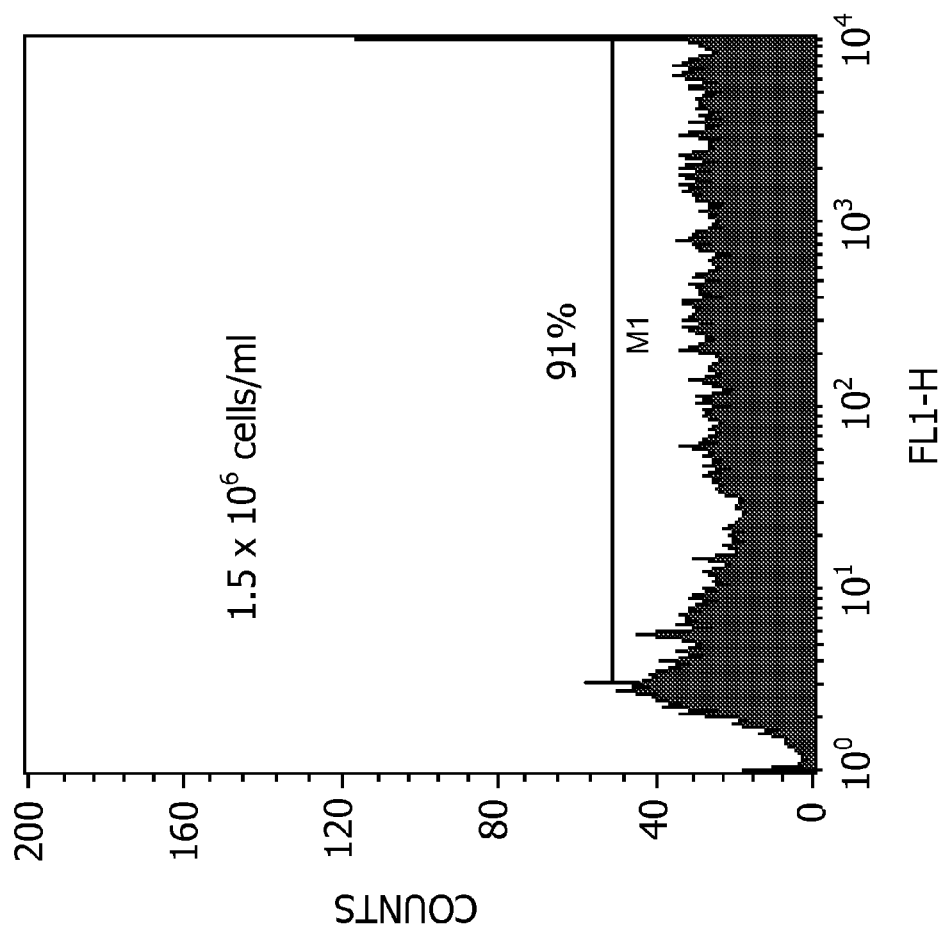

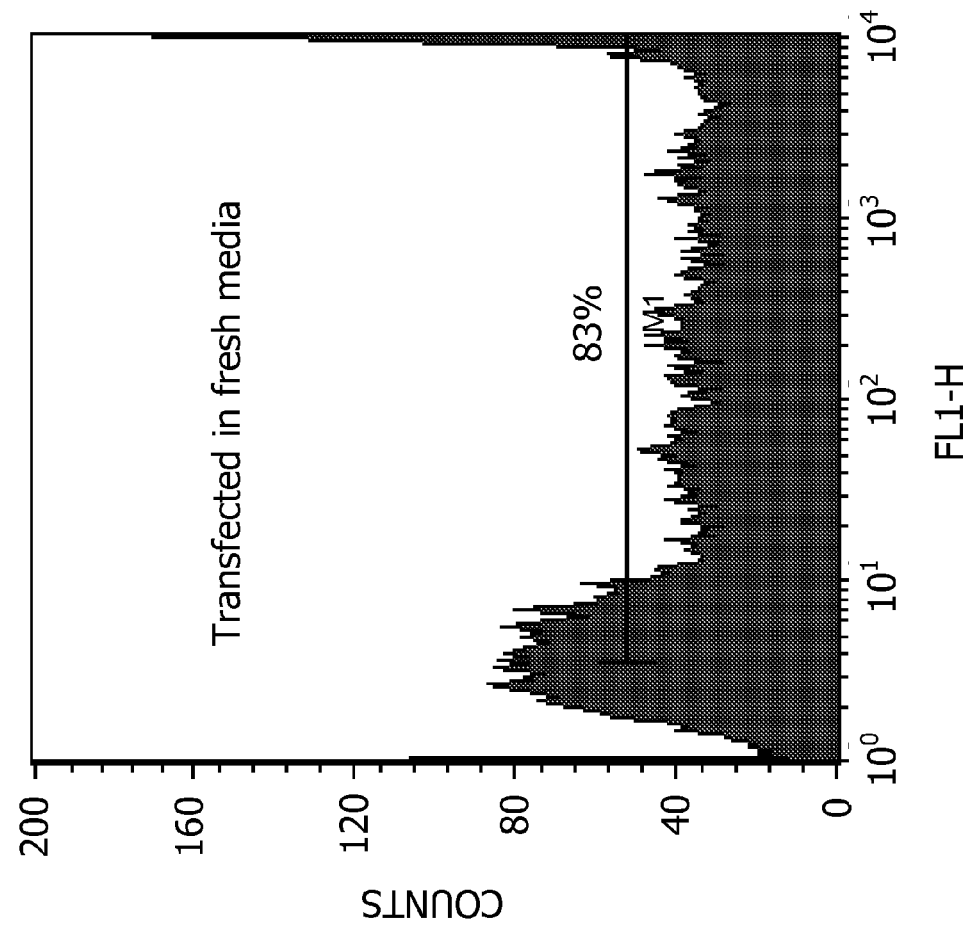

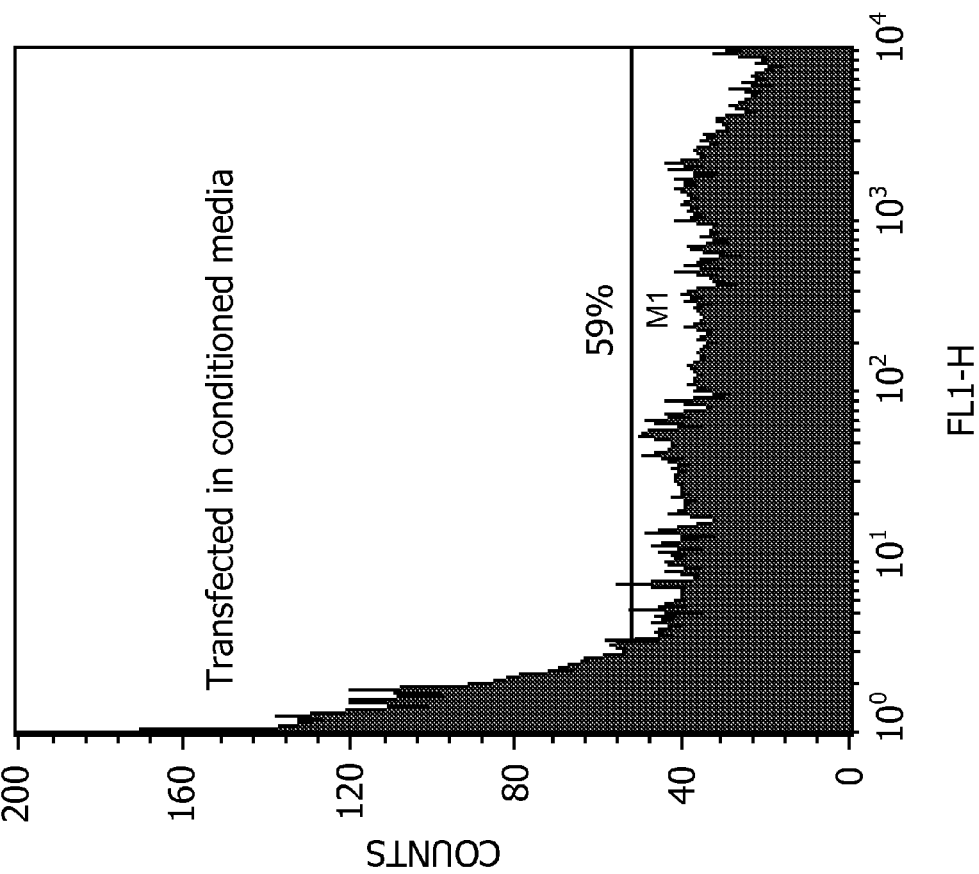

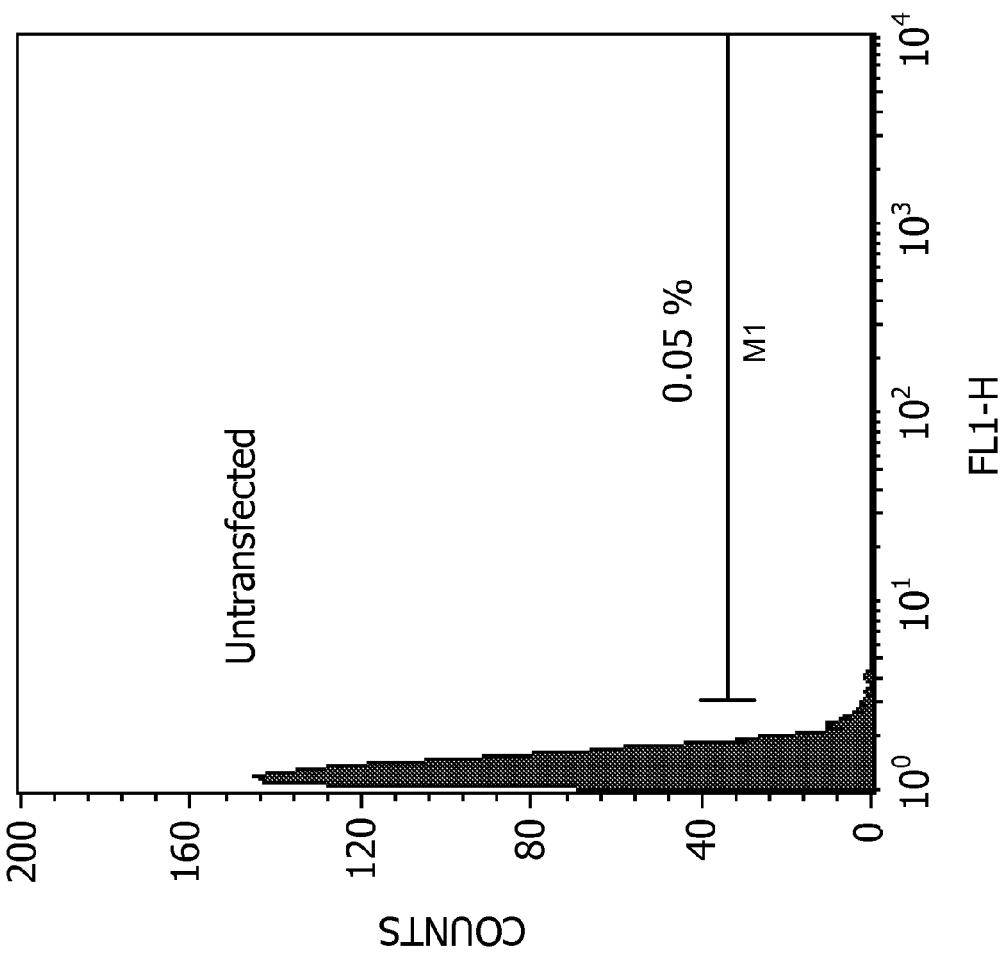

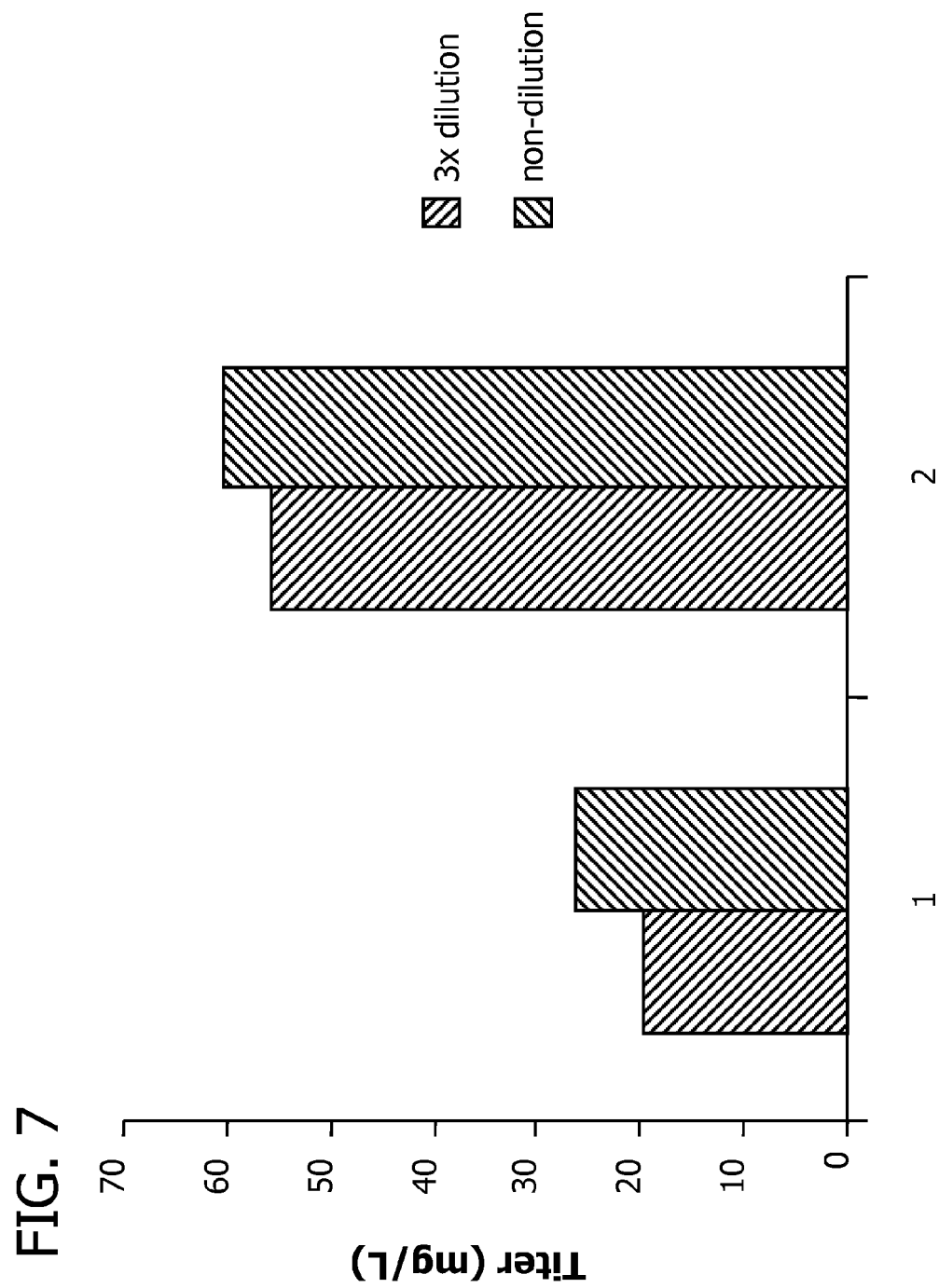

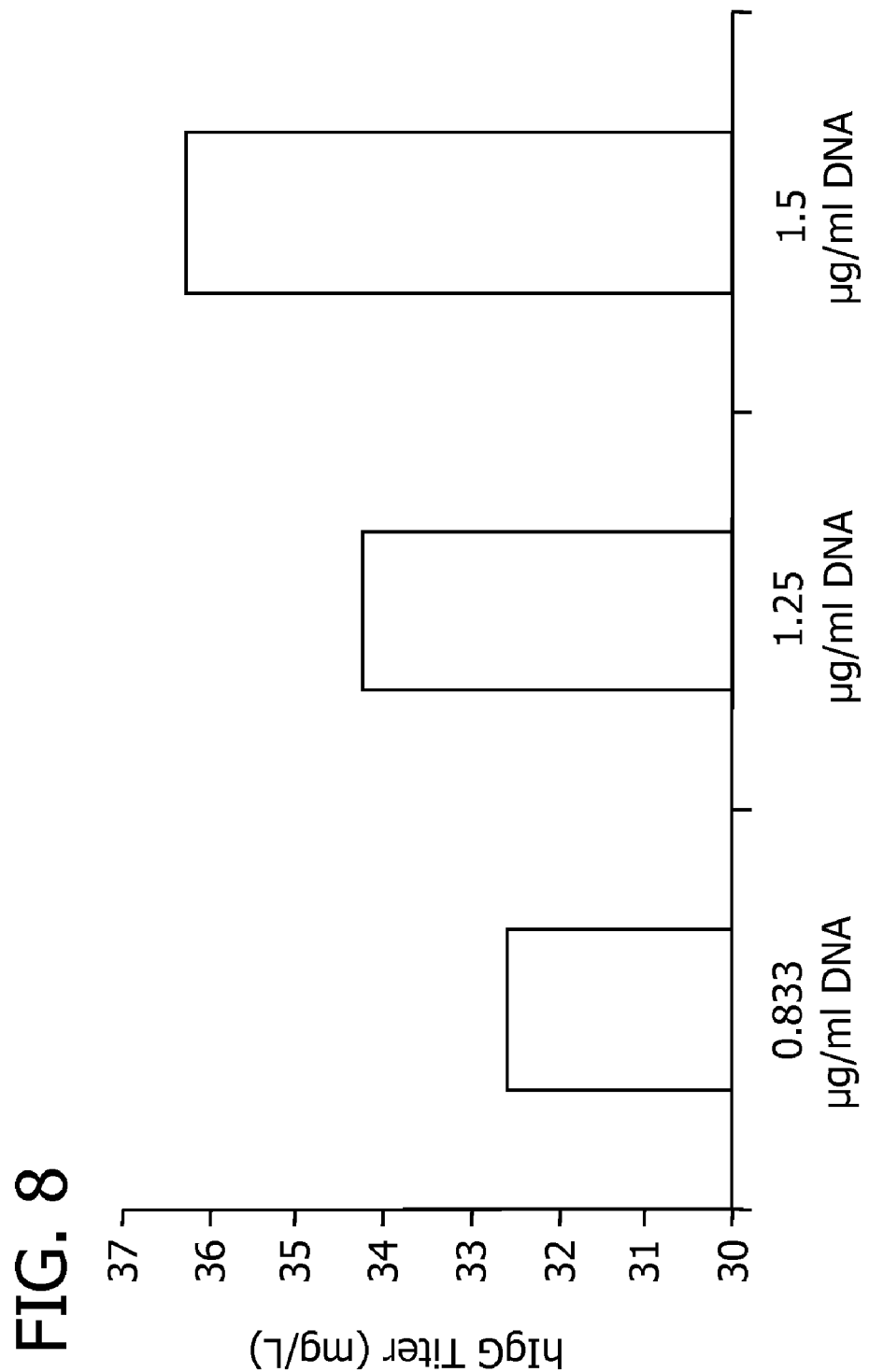

PROCESSES AND COMPOSITIONS FOR TRANSFECTING CHINESE HAMSTER OVARY (CHO) CELLS

CROSS-REFERENCE TO RELATED APPLICATIONS

This is a non-provisional patent application claiming priority from U.S. Provisional Patent Application Ser. Nos. 60/846,664 filed Sep. 22, 2006; 60/843,186 filed Sep. 8, 2006; 60/802,914 filed May 24, 2006; and 60/802,041 filed May 19, 2006, each of which is incorporated herein by reference in its entirety.

FIELD OF THE INVENTION

The present invention generally relates to processes and compositions for the transfection of Chinese hamster ovary (CHO) cells. More specifically, the present invention relates to processes for the transfection of CHO cells suspended in an aqueous medium using a transfection composition containing nucleic acid and a polycationic composition.

BACKGROUND OF THE INVENTION

A variety of strategies are available for the delivery of genes into cells. Transfection, in particular, refers to the delivery or transfer and uptake of nucleic acids into cultured cells mediated by gene transfer techniques. Commonly utilized transfection techniques generally tend to fall within two categories: transfection by physical methods (e.g., biolistic particle delivery and electroporation) and transfection by biochemical methods.

Biochemical methods of transfection have been used for a number of years to deliver nucleic acids into cultured cells. Such techniques may involve, for example, the use of inorganic aggregates (e.g., calcium-phosphate-mediated transfection), cationic polymers (e.g., diethylaminoethyl (DEAE)-dextran-, polylysine-, or polybrene-mediated transfection) and, more recently, cationic lipid (liposome) reagents (e.g., Lipofectamine™, Invitrogen, Carlsbad, Calif.). Other polycationic macromolecules and/or amphiphilic aggregates have also been developed which ionically condense nucleic acids and bind to the cell surface (see, e.g., Cotton et al., Curr. Opin. Biotechnol. (1993), 4, 705-710; Frese et al., Adv. Drug Delivery Rev. (1994), 14, 137-152; Haensler et al., Bioconjugate Chem. (1993), 4, 372-379; Behr et al., Bioconjugate Chem. (1994), 5, 382-389; Legendre et al., Proc. Natl. Acad. Sci. USA (1993), 90, 893-897). One particular polycationic composition, polyethyleneimine, has been shown to be a relatively efficient vehicle for delivering nucleic acids to cells both in vivo and in vitro (see, e.g., Boussif et al., Proc. Natl. Acad. Sci. USA (1995), 92, 7297-7301).

Polyethyleneimine is an organic macromolecule having a relatively high cationic charge density potential. Thus, it readily binds and condenses nucleic acids into small condensates which can be taken up (i.e., endocytosed) by cells. Additionally, every third atom of polyethyleneimine is an amino moiety that can be protonated; thus, the polymeric network can act as a "proton sponge" at a variety of pH's, using the hydrogen ion buffering polyamines to absorb hydrogen ions during the acidification of the endosome which leads to endosome lysis. See, e.g., Boussif et al., supra; Horbinski et al., BMC Neuroscience (2001), 2, 2.

The use of mammalian cell lines for recombinant gene expression provides a number of advantageous features such as proper folding and post-translational modification of the recombinant polypeptides. Chinese hamster ovary (CHO) cells, in particular, are a frequently used host cell for the production of recombinant polypeptides that require post-translational modification to express full biological function.

Derouazi et al. (Biotechnol. Bioeng. (2004), 87(4), 537-545) disclose cultivating CHO cells from the CHO-DG44 cell line in a serum-free, chemically defined medium and transfecting them using a transfection agent including linear or branched polyethyleneimine and DNA. In particular, Derouazi et al. disclose seeding the CHO cells in a 3 L bioreactor at a cell density of $2 \times 10^6$ cells/ml of cell culture medium. Immediately after seeding, the cells were transfected with the polyethyleneimine/DNA mixture, which was formed by diluting DNA and polyethyleneimine separately in 150 mM NaCl or 278 mM glucose and adding the polyethyleneimine dilution to the DNA dilution to form the transfection agent.

Although the above-described techniques and processes are generally useful for the transfection and expression of recombinant polypeptides in CHO cells, there are limitations on their effectiveness, including, for example, limited transfection efficiency and lower amounts of recombinant polypeptide expressed and/or produced by the transfected CHO cells, particularly in the large-scale culture and transfection of CHO cells. As a result of lower transfection efficiency, for instance, a lower amount of recombinant polypeptide may be expressed by the CHO cells. Accordingly, a need remains for additional processes for the transfection of CHO cells having improved transfection efficiencies and/or greater recombinant polypeptide production and/or expression by the transfected CHO cells.

SUMMARY OF THE INVENTION

Among the various aspects of the present invention are processes for transfecting Chinese hamster ovary (CHO) cells suspended in an aqueous medium. These processes enable optimization of transfection at a variety of culture volumes and enable high efficiency delivery of nucleic acid into CHO cells and greater recombinant polypeptide production by the transfected CHO cells.

Briefly, therefore, the present invention is directed to a process for transfecting CHO cells suspended in an aqueous medium. The process comprises combining a population of CHO cells suspended in an aqueous medium with a transfection composition comprising linear polyethyleneimine and nucleic acid and having an effective average diameter and a polydispersity about this average of less than 0.4.

The present invention is also directed to a composition for transfecting Chinese hamster ovary (CHO) cells. The transfection composition contains linear polyethyleneimine and nucleic acid and has an effective average diameter and a polydispersity about this average of less than 0.4.

The present invention is also directed to a process for forming a transfection composition for Chinese hamster ovary (CHO) cells. The process comprises combining linear polyethyleneimine and nucleic acid in an aqueous medium having a pH of at least 5.8 and incubating the combination to form a transfection composition containing the linear polyethyleneimine and nucleic acid and having an effective average diameter and a polydispersity about this average of less than 0.4.

Other objects and features will be in part apparent and in part pointed out hereinafter.

BRIEF DESCRIPTION OF THE DRAWINGS

FIGS. 1A, 1B, 1C, 1D, 1E, and 1F are flow cytometry histograms showing GFP expression of transfected CHO cells 48 hours after transfection with 2.5 µg/ml pEGFP-C1 and 25 kDa linear polyethyleneimine using varying N/P ratios. The histograms show live gated cells; M1 gates showing the percent GFP positive cells were drawn using untransfected cells to set the negative threshold. See Example 1.

FIGS. 3A, 3B, 3C, 3D, and 3E are flow cytometry histograms showing GFP expression of transfected CHO cells 48 hours after transfection with 2.5 µg/ml pEGFP-C1 and 25 kDa linear polyethyleneimine using particles formed in HEPES-buffered saline with a pH of 7.3 and with an N/P ratio of 23:1. In FIG. 3A, the CHO cells were grown to a density of about $4 \times 10^5$ cells/ml of the aqueous medium prior to transfection. In FIG. 3B, the CHO cells were grown to a density of about $1 \times 10^6$ cells/ml of the aqueous medium prior to transfection. In FIG. 3C, the CHO cells were grown to a density of about $1.5 \times 10^6$ cells/ml of the aqueous medium prior to transfection. In FIG. 3D, the CHO cells were grown to a density of about $2 \times 10^6$ cells/ml of the aqueous medium prior to transfection. In FIG. 3E, the CHO cells were grown to a density of about $4 \times 10^6$ cells/ml prior to transfection. In each of FIGS. 3A, 3B, 3C, 3D, and 3E, the CHO cells were transfected at a cell density of about $2 \times 10^6$ cells/ml of the aqueous medium, and cell density was diluted 3-fold at about 4 hours after transfection. See Example 3.

FIGS. 4B and 4C are flow cytometry histograms showing GFP expression of transfected CHO cells 48 hours after transfection with 2.5 µg/ml pEGFP-C1 and 25 kDa linear polyethyleneimine using particles formed in HEPES-buffered saline with a pH of 7.3 and with an N/P ratio of 23:1. In FIG. 4B, the CHO cells were centrifuged and resuspended in fresh aqueous medium prior to transfection. In FIG. 4C, the CHO cells were centrifuged and resuspended in conditioned media (i.e., the same media that the cells had grown in for about 48 hours). See Example 4.

FIG. 6A is a flow cytometry histogram showing untransfected CHO cells showing no GFP expression.

FIG. 7 is a graph of the titer from an antibody production run. The graph shows two experimental runs comparing the dilution of the CHO cells with an aqueous media after transfection versus no dilution of the CHO cells after transfection. See Example 7.

FIG. 8 is a graph of the titer from an antibody production run. The graph shows three experimental runs comparing three different concentrations of nucleic acid used in the transfection composition. In the three experimental runs, the density of the population of CHO cells was not diluted after transfection. See Example 8.

ABBREVIATIONS AND DEFINITIONS

Figure 1B:
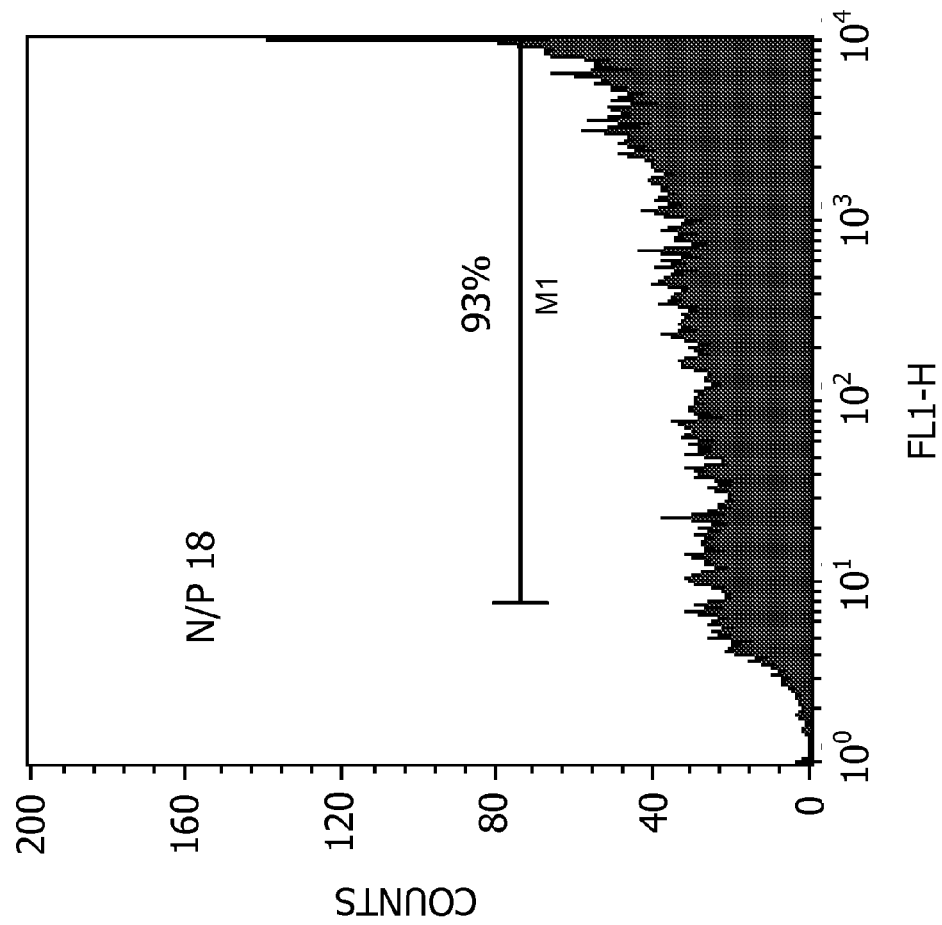

The following definitions and methods are provided to better define the present invention and to guide those of ordinary skill in the art in the practice of the present invention. Unless otherwise noted, terms are to be understood according to conventional usage by those of ordinary skill in the relevant art.

The term "nucleic acid" as used herein generally refers to a molecule or strand of DNA, RNA, or derivatives or analogs thereof including one or more nucleobases. Nucleobases include purine or pyrimidine bases typically found in DNA or RNA (e.g., adenine, guanine, thymine, cytosine, and/or uracil). The term "nucleic acid" also includes oligonucleotides and polynucleotides. Nucleic acids may be single-stranded molecules, or they may be double-, triple- or quadruple-stranded molecules that may include one or more complementary strands of a particular molecule.

As used herein, "polynucleotide" and "oligonucleotide" are used interchangeably and mean a polymer of at least two nucleotides joined together by phosphodiester bonds and may consist of either ribonucleotides or deoxyribonucleotides.

The term "polypeptide" when used herein refers to two or more amino acids that are linked by peptide bond(s), regardless of length, functionality, environment, or associated molecule(s). Typically, the polypeptide is at least four amino acid residues in length and can range up to a full-length protein. As used herein, "polypeptide," "peptide," and "protein" are used interchangeably.

As used herein, "sequence" means the linear order in which monomers occur in a polymer, for example, the order of amino acids in a polypeptide or the order of nucleotides in a polynucleotide.

As used herein, "transfect," "transfection," and "transfecting" refer to the delivery or transfer and uptake of nucleic acids into cultured cells. It will be understood by one of skill in the art that the terms "transfect," "transfection," and "transfecting" encompass both the "stable" and the "transient" transfection of cultured cells. In transient transfection, for example, recombinant nucleic acid is introduced into a cell to obtain the temporary expression of the target gene. Because the nucleic acid is typically not stably integrated into the chromosome of the host cell, the nucleic acid is eventually degraded or catabolized by nucleases, or is diluted by cell division. Alternatively, in stable or permanent transfection, the cells are co-transfected with an additional gene that provides some selection advantage, allowing the few cells that happen to have the desired gene incorporated into its genome to be selected and proliferated over a period of time until the culture substantially consists of only the cells that permanently express the desired gene. As between stable and transient transfection methods, therefore, the initial delivery or transfer and uptake of nucleic acid, is essentially the same.

See, e.g., Sambrook et al. (2001), "Molecular Cloning, A Laboratory Manual," 3d ed., Cold Spring Harbor Laboratory Press.

Various embodiments of the present invention rely on altering biological material using molecular techniques. Molecular techniques refers to procedures in which nucleic acid is manipulated in a test tube during at least one stage of the process, such as the direct manipulation of DNA or the use of shuttle host such as bacterium. Additional examples of molecular techniques include, for example, methods of using PCR to multiply a nucleic acid of interest for introduction and expression in a mammal or mammal cell via expression vectors or direct introduction of the nucleic acid; methods of using nucleic acid libraries to determine, isolate, introduce, and express a nucleic acid of interest into a mammal or mammalian cell via expression vectors or direct introduction of the nucleic acid; isolation of nucleic acid segments, concatemerization of said nucleic acid segments into a larger nucleic acid, introduction, and expression of the same in a mammal or mammalian cell via expression vectors or direct introduction of the nucleic acid; and isolation of mRNA from a gene, creation of cDNA from the mRNA by reverse transcription, and introduction and expression of the same in a mammal or a cell via expression vectors or direct introduction of the nucleic acid. Such methods are well known in the art and are described in, for example, Sambrook et al. (2001), supra.

DETAILED DESCRIPTION OF THE INVENTION

The present invention is generally directed to improved processes for transfecting Chinese hamster ovary (CHO) cells. Surprisingly, it has been found that the efficiency of nucleic acid delivery to CHO cells using a polycationic composition comprising linear polyethyleneimine as the transfection vehicle can be increased and/or subsequent polypeptide production from the transfected CHO cells improved by optimizing one or more features of conventional transfection techniques.

Transfection efficiency and/or polypeptide production from the transfected CHO cells may be increased, for example, by transfecting the CHO cells when they are in the log phase of growth (e.g., the early, mid-, or late log phase of growth), by concentrating the density of CHO cells prior to transfection, and/or by optimizing the process by which the transfection composition is formed. Advantageously, transfection efficiencies in the range of 70% to 90%, routinely greater than 90%, greater than 95%, and, in some cases, as high as 99.9% can be obtained in the transfection of CHO cells according to the processes described herein. Additionally or alternatively, relatively high levels of polypeptide can be produced by the CHO cells transfected according to the processes described herein. These transfection efficiencies and/or polypeptide production levels can be obtained for CHO cells suspended in culture volumes from a fraction of a liter to tens of thousands of liters.

One aspect of the present invention, therefore, is directed to processes for the transfection of CHO cells cultured in suspension in an aqueous medium. In general, the processes involve preparing the CHO cells for transfection by culturing the CHO cells in an aqueous medium and transfecting the CHO cells with a transfection composition containing nucleic acid and a polycationic composition comprising linear polyethyleneimine. Following transfection, the CHO cells are typically maintained in culture such that polypeptide(s) produced and/or expressed by the transfected CHO cells may be analyzed and/or recovered.

The transfection composition may be presented to the CHO cells in the form of an aqueous transfection reagent containing an aqueous medium and a population of particles, the particles comprising the nucleic acid and a polycationic composition comprising linear polyethyleneimine dispersed in the aqueous medium. In one embodiment, the linear polyethyleneimine is at least a component of the polycationic composition for at least a fraction of the population of particles; that is, some particles may contain a mixture of linear polyethyleneimine and another polycationic composition, some particles may contain only linear polyethyleneimine, and some particles may contain no linear polyethyleneimine. For instance, two or more subpopulations of particles may be present, one subpopulation of particles containing only linear polyethyleneimine as the polycationic composition and the other subpopulation(s) of particles containing a different polycationic composition or a mixture of polycationic compositions (which may or may not include linear polyethyleneimine). Typically, linear polyethyleneimine is at least a component of the polycationic composition for a predominant population of the particles. Preferably, linear polyethyleneimine is at least a component of the polycationic composition for substantially all of the particles.

Preparation of the CHO Cells for Transfection

In general, any CHO cell line that can be cultured in suspension may be used as the host cell, including CHO cell derivatives and/or genetic variants. For example, a CHO cell line that has previously been modified (e.g., by stable transfection) to overexpress or underexpress certain receptors or genes may be transfected according to the processes described herein.

Exemplary CHO cell lines which may be transfected include, but are not limited to, the CHO-K1, CHO-K1SV, CHO-DG44, CHO-DUKX-B11, CHO-Pro5, CHO-SSF, CHO-F3B4, CHO-hERG, and CHO-S cell lines, and derivatives and/or genetic variants thereof, each of which and others may be or have previously been adapted for culture in suspension using conventional methods. See, e.g., Puck et al., J. Exp. Med. (1958), 108, 945-956; Urlaub et al., Proc. Natl. Acad. Sci. USA (1980), 77, 4216-4220; Kao et al., Proc. Nat. Acad. Sci. USA (1968), 60, 1275; D'Anna, J. A., Methods Cell Sci. (1996), 18, 115; Deaven et al., Chromosoma (1973), 41, 129; D'Anna et al., Radiation Research (1997), 148, 260; Stanley et al., Cell (1975), 6, 121; and the like.

The CHO cells are prepared for transfection by culturing the cells in suspension in an aqueous medium according to conventional techniques known to those of skill in the art. Standard cell culture conditions for the suspension culture of CHO cells (e.g., agitation, temperature, pH, humidity, $CO_2$ level, dissolved $O_2$ level, and the like) may also be employed. For example, CHO cells are commonly cultured in suspension in an agitated aqueous medium generally having a pH of between about 7.0 and about 7.5. Further, CHO cells are commonly cultured at 37° C. in a humidified 5-8% $CO_2$ atmosphere with a dissolved $O_2$ level of about 30-90% of air saturation. Favorable culture techniques and conditions for any given CHO cell line are generally known, or may be readily determined by one of skill in the art.

The CHO cells are preferably cultured in an aqueous suspension medium. The aqueous medium typically includes a cell culture media system (i.e., a basal cell culture media optionally supplemented with one or more additional nutrients or other components). Conventional cell culture media systems for culturing CHO cells in suspension are known in the art, and generally include components that assist in the growth and proliferation of the CHO cells. For example, the cell culture media system may include a pH buffer to maintain the pH within an appropriate range (e.g., 7.0 to 7.5). Common pH buffers for use in cell culture media systems include, for example, carbonates, chlorides, sulfates, phosphates, N-[2-hydroxyethyl]piperazine-N'-[2-ethanesulfonic acid] (HEPES) buffer, 3-[N-morpholino]-propanesulfonic acid (MOPS) buffer, and the like. The cell culture media system may also include any number of nutrients such as monosaccharides (e.g., mannose, fructose, galactose, maltose, and glucose); amino acids (e.g., arginine, cysteine, glutamine, lysine, and valine); and vitamins (e.g., pyridoxine ($B_6$), cyanocobalamin ($B_{12}$), biotin (K), ascorbic acid (C), and riboflavin ($B_2$)). Further, the cell culture media system may include an osmolality regulator (e.g., salts such as NaCl, KCl, and $KNO_3$), non-ferrous metal ions (e.g., magnesium, copper, zinc, sodium, potassium, and selenium), antibiotics (e.g., ampicillin, penicillin, streptomycin, neomycin, nystatin, kanamycin, gentimycin, and combinations thereof), and water.

The CHO cells are preferably cultured in an aqueous medium that is substantially free of components that can interfere with the efficient transfection of the CHO cells, and/or interfere with the subsequent production, recovery, purification, and/or use of polypeptide(s) expressed by the transfected CHO cells. For example, a serum-free and human-, animal-, and plant-derived component-free aqueous medium is generally preferred because its use facilitates the downstream processing of products from the transfected CHO cells (e.g., polypeptides secreted or released from the cells). Additionally, serum is an expensive commodity, and its composition can vary from lot to lot. Moreover, regulatory agencies have expressed concerns about the contamination potential of recombinant human therapeutics with adventitious agents (e.g., viruses, mycoplasma, and the like) that may be present in human- or animal-derived products. Further, plant-derived components such as lysates and hydrolysates tend to be charged components than can adversely affect transfection efficiencies. Thus, in one embodiment the aqueous medium is substantially free of serum, protein, lysates, hydrolysates, human-, animal-, and plant-derived components, and combinations thereof. Still more preferably, the aqueous medium comprises a chemically-defined cell culture media system; that is, the media is substantially free of serum, protein, lysates, hydrolysates, human-, animal-, and plant-derived components, and all or substantially all of the components included in the media have a known chemical structure. Generally, CHO cells may be adapted to grow in serum-free and human-, animal-, and plant-derived component-free media according to conventional methods. See, e.g., Schifferli et al., Focus (1999), 21, 16; Sinacore et al., Biotechnol. Bioeng. (1996), 52(4), 518-528; Ham et al., Proc. Natl. Acad. Sci. USA (1965), 53, 288.

The aqueous suspension medium used in the preparation of the CHO cells for transfection is also preferably substantially free of anti-clumping agents (i.e., agents used to decrease cell-to-cell aggregation and/or cell attachment to culture vessels such as, for instance, dextran sulfate, pentosan polysulfate, ethylenediaminetetraacetic acid and salts thereof, combinations thereof, and the like). Thus, the aqueous medium in which the CHO cells are cultured prior to transfection typically includes less than 0.1% (w/v) of an anti-clumping agent. For example, the aqueous medium may include less than 0.09%, less than 0.08%, less than 0.07%, or less than 0.06% (w/v) of an anti-clumping agent. In various embodiments, the aqueous medium includes less than 0.05% (w/v) of an anti-clumping agent; more preferably in these embodiments less than 0.025% (w/v). In a particular embodiment, the aqueous medium includes less than 0.01% (w/v) of an anti-clumping agent. The aqueous suspension medium used in the preparation of the CHO cells for transfection also typically includes less than 0.1% (w/v) of other cell protectants such as, for example, polyethylene glycol, polyvinyl alcohol, and pluronic polymers (e.g., Pluronic® F-68). For example, the aqueous medium may include less than 0.09%, less than 0.08%, less than 0.07%, or less than 0.06% (w/v) of a cell protectant. In various embodiments, the aqueous medium includes less than 0.05% (w/v) of a cell protectant; more preferably in these embodiments less than 0.025% (w/v). In a particular embodiment, the aqueous medium includes less than 0.01% (w/v) of a cell protectant. In general, anti-clumping agents and cell protectants tend to adversely affect transfection efficiency. For example, conventional anti-clumping agents (e.g., dextran sulfate or pentosan polysulfate), tend to be highly charged polyanionic compounds that can compete with polycationic nucleic acid delivery vehicles such as linear polyethyleneimine for CHO cell binding and/or induce dissociation of the polycationic nucleic acid delivery vehicles, resulting in a reduction in transfection efficiency. After transfection is complete, however, it may be desirable to include anti-clumping agents and/or other cell protectants in the aqueous medium to maximize the growth and viability of the transfected CHO cells.

Suitable cell culture media systems and components thereof for suspension-grown CHO cells are available from a variety of vendors such as, for example, Invitrogen (Carlsbad, Calif.), Sigma-Aldrich Co. (St. Louis, Mo.), and HyClone (Logan, Utah). One particularly preferred cell culture media system includes Freestyle™ CD17 cell culture media and 8 mM L-glutamine, and is substantially free of anti-clumping agents and includes less than about 0.01% (w/v) Pluronic® F-68. The cell culture media system may optionally include an antibiotic such as, for example, ampicillin, penicillin, streptomycin, neomycin, nystatin, kanamycin, gentimycin, combinations thereof, and the like.

The CHO cells may be cultured, transfected, and maintained in culture post-transfection in a batch system. In a batch culture system, the culture is generally initiated by inoculating or seeding cells to the aqueous suspension medium, but without the subsequent inflow of cell culture nutrients (e.g., monosaccharides and amino acids). There is also typically no systematic addition or systematic removal of culture media and/or cells (e.g., by passing or splitting) from the culture system in a batch culture system. The concentration of nutrients and metabolites in the cell culture medium are generally dependent on the initial concentrations employed within the batch and the subsequent alteration of the cell culture media, e.g., by the uptake of nutrients by the cells.

Alternatively, the CHO cells may be cultured, transfected, and maintained in culture post-transfection in a fed-batch system. In a fed-batch culture system, cell culture media and/or nutrients, commonly in a solid or concentrated liquid form, are added to the culture system either periodically or continuously before, during, and/or after transfection. Similar to batch culture, a fed-batch culture may be initiated by inoculating or seeding cells to the aqueous suspension medium, but, in contrast to a batch culture, there is a subsequent inflow of cell culture nutrients to the culture system, such as by way of a concentrated nutrient feed. Like batch culture systems, there is also typically no systematic removal of culture media and/or cells (e.g., by passing or splitting) from the culture system in a fed-batch culture system. Fed-batch culture systems can be advantageous in certain applications where it may be desirable to monitor and manipulate the levels of various analytes in the culture medium and/or maximize the viability and the length of time of growth and density of the transfected CHO cells, since the concentration of nutrients and metabolites in the culture media can be readily controlled or affected by altering the composition of the nutrient feed. The nutrient feed delivered to a fed-batch culture system is typically a concentrated nutrient solution comprising a monosaccharide (e.g., glucose) and an amino acid (e.g., L-glutamine), and may optionally contain other conventional cell culture media components such as pH buffers, salts, vitamins, and the like. The nutrient feed is typically concentrated to minimize the increase in culture volume while supplying sufficient nutrients for continued cell growth.

Once transfected, the CHO cells are generally allowed to grow until they have used up all the nutrients in the cell culture media (e.g., in batch culture systems) and/or until they have reached a maximum density, after which growth becomes arrested and the cells begin to die, due to either exhaustion of the nutrients or accumulation of an inhibitor to growth. In a particular embodiment, the cells are cultured, transfected, and maintained in culture post-transfection in a bioreactor; more preferably in this embodiment the CHO cells are cultured, transfected, and maintained in culture post-transfection in a fed-batch culture system. Suitable bioreactor systems are described in further detail below.

The CHO cells generally have a minimum seeding density at which they are initially cultured in suspension; the minimum seeding density may vary depending on the particular CHO cell line employed. The seed density may also depend on the cell culture conditions and cell culture media components, and/or a variety of other factors. By way of example, CHO-S cells generally have a minimum seeding density of about $1 \times 10^5$ to about $2 \times 10^5$ cells/ml of the aqueous medium.

After seeding, the CHO cells are preferably allowed to adjust to the culture medium and/or conditions; that is, the CHO cells are not transfected immediately after seeding. During this period of time (i.e., the lag phase of growth) the cell population typically divides at a rate less than the standard exponential rate of division for that particular CHO cell line. The CHO cells are maintained at the conditions described above (e.g., 37° C., 5-8% $CO_2$), and eventually the population of CHO cells in culture will enter the exponential or log phase of growth. The log phase of growth is the pattern of balanced growth wherein the cells are dividing regularly, and the population of cells is growing by geometric progression (e.g., $2^0$, $2^1$, $2^2$, $2^3$, etc., ... $2^n$, where n is the number of generations). The CHO cells will generally divide at a constant rate depending upon such factors as the composition of the cell culture media system, the culture conditions, the particular CHO cell line, and the like. In any cell culture system, the density of a population of CHO cells entering into the log phase of growth may vary depending on the particular CHO cell line employed, the vessel in which the CHO cells are cultured, and/or depending on a variety of other factors, such as cell culture conditions and cell culture media components. By way of example, CHO-S cells typically have a density of about $3 \times 10^6$ to about $4 \times 10^6$ cells/ml of the aqueous medium when they enter the exponential or log phase of growth.

As the cell culture components and nutrients can generally only be limitedly renewed by supplementation (e.g., as in a fed-batch system), exponential growth of the CHO cells post-transfection is typically limited to a few generations (e.g., about 6 generations). Eventually, waste products from the CHO cells (e.g., the transfected CHO cells) accumulate in the aqueous medium, the CHO cells reach a maximum density, and/or the CHO cells exhaust one or more essential nutrients in the aqueous medium. At this point the cells typically exit the log phase of growth and enter the stationary phase, a growth plateau during which time there is little or no change in the number of viable cells (i.e., some of the CHO cells will die, while others will continue dividing). Similar to the seeding density and the density of the population of CHO cells entering into the log phase of growth, the density of the population of CHO cells at the time they exit the log phase of growth can vary depending on the particular CHO cell line employed, the vessel in which the CHO cells are cultured, and/or depending on a variety of other factors such as cell culture conditions and cell culture media components. Accordingly, the density of the population of CHO cells at the time they exit the log phase of growth may be a few million cells to tens of millions of cells/ml of the aqueous medium. By way of example, CHO-S cells grown in shake flasks typically have a density of about $5 \times 10^6$ cells/ml of the aqueous medium when they exit the log phase of growth, whereas the density of CHO-S cells when they exit the log phase of growth could be as much as about twice this amount, or higher, when the cells are cultured in a bioreactor. Thus, the cell density at which a population of CHO cells exits the log phase may be dependent, in part, upon the particular CHO cell line, the cell culture medium and components and concentrations thereof, vessel volume, and related environmental conditions.

The CHO cells are desirably in an active mitotic stage at the time they are transfected. Thus, the CHO cells are preferably transfected when the population of CHO cells is in the log phase of growth (i.e., dividing at an exponential rate). The log phase of growth generally includes the early, mid-, and late log phases of growth. One of skill in the art can readily determine the phase of growth a population of cultured CHO cells are in (e.g., lag, log (including early, mid-, and late log), stationary, or death phase), for example, by monitoring the changes in the density of the CHO cells in the cultured population over a period of time.

The CHO cells are generally transfected when the population of CHO cells is in the early log phase of growth. A population of CHO cells in the early log phase of growth is typically characterized as having a density that is less than 50% of the difference between (a) the density of the CHO cells when they enter the log phase of growth and (b) the density of the CHO cells when they exit the log phase of growth, under the conditions in which the cells are being grown (i.e., the particular CHO cell line, the cell culture medium and components and concentrations thereof, vessel volume, and related environmental conditions). By way of example, the CHO cells may be in the early log phase of growth when the population of CHO cells has a density that is less than 45%, less than 35%, less than 25%, or less than 15% of the difference between (a) and (b) above. In some instances, the CHO cells may be in the early log phase of growth when the density of the population of CHO cells is less than 10%, less than 7.5%, or less than 5% of the difference between (a) and (b) above. It appears that by transfecting CHO cells when the population is in the early log phase of growth, transfection efficiency and/or polypeptide production from the resulting transfected cells is substantially improved (see Example 3). While the transfection of CHO cells in the mid- to late log phase of growth according to the processes of the present invention provide improved transfection efficiency and/or improved polypeptide production over conventional methods, it has been found that transfecting CHO cells when the population of CHO cells is in the early log phase of growth is generally preferred.

In general, all variants of CHO cells adapted for suspension growth will possess similar growth characteristics. Thus, for example, any given CHO cell line may have (a) a density of about $3.5 \times 10^6$ cells/ml of the aqueous medium when they enter the log phase of growth and (b) a density of about $5 \times 10^6$ cells/ml of the aqueous medium when they exit the log phase of growth. The difference between the two densities (i.e., (b) the density of the CHO cells when they exit the log phase of growth minus (a) the density of the CHO cells when they enter the log phase of growth), therefore, is about $4.65 \times 10^6$ cells/ml of the aqueous medium. Accordingly, the CHO cells may be in the early log phase of growth and transfected or concentrated in preparation for transfection when the cells have reached a density of, e.g., about $2.33 \times 10^6$; about $1.53 \times 10^6$; about $1.16 \times 10^6$; about $0.7 \times 10^6$; or about $4.65 \times 10^5$ cells/ml of the aqueous medium, that is, about 50%, about 33%, about 25%, about 15%, or about 10%, respectively, of $4.65 \times 10^6$ cells/ml of the aqueous medium (i.e., the difference between (a) the density of the CHO cells when they enter the log phase of growth and (b) the density of the CHO cells when they exit the log phase of growth).

Irrespective of the particular stage of the log phase of growth the CHO cells are in (i.e., early, mid-, or late log phase), in various embodiments the CHO cells are transfected when the density of the population of CHO cells is from about $0.5 \times 10^6$ to about $3 \times 10^6$ cells/ml of the aqueous medium. For example, the CHO cells may be transfected when the density of the population of CHO cells is about $0.75 \times 10^6$, about $1 \times 10^6$, about $1.25 \times 10^6$, about $1.5 \times 10^6$, about $1.75 \times 10^6$, about $2 \times 10^6$, about $2.25 \times 10^6$, about $2.5 \times 10^6$, or about $2.75 \times 10^6$ cells/ml of the aqueous medium. By way of another example, the CHO cells may be transfected when the density of the population of CHO cells is from about $0.5 \times 10^6$ to about $1.5 \times 10^6$, from about $0.75 \times 10^6$ to about $1.25 \times 10^6$, from about $0.8 \times 10^6$ to about $1.2 \times 10^6$, from about $0.85 \times 10^6$ to about $1.15 \times 10^6$, or from about $0.9 \times 10^6$ cells/ml of the aqueous medium. By way of another example, the CHO cells may be transfected when the density of the population of CHO cells is from about $1.5 \times 10^6$ to about $2.5 \times 10^6$, from about $1.75 \times 10^6$ to about $2.25 \times 10^6$, from about $1.8 \times 10^6$ to about $2.2 \times 10^6$, from about $1.85 \times 10^6$ to about $2.15 \times 10^6$, or from about $1.9 \times 10^6$ to about $2.1 \times 10^6$ cells/ml of the aqueous medium.

In some instances (e.g., for GFP or other reporter gene expression), the density of the CHO cells is preferably concentrated prior to transfection; that is, the density of the population of CHO cells is increased from a lesser cell density to a greater cell density per volume of the aqueous media. It appears that by transfecting the CHO cells at a cell density more commonly observed in the mid- to late log phase (or later), but with the growth characteristics of early to mid-log phase, a higher percentage of the CHO cells will come into contact with and/or take up (i.e., endocytose) the nucleic acid in the transfection composition, resulting in an improved transfection efficiency. In other instances (e.g., for larger-scale polypeptide production), concentration of the cell density is less desired; that is, the CHO cells may be cultured until they reach a desired density and transfected at that density without a cell density concentration step.

Where the CHO cells are concentrated prior to transfection, the density of CHO cells in the aqueous medium (e.g., the CHO cells in the log phase of growth or, more preferably, the CHO cells in the early log phase of growth as described above) is typically concentrated to a density of from about $0.5 \times 10^6$ to about $3 \times 10^6$ cells/ml of the aqueous medium prior to transfection. Thus, for example, the density of the CHO cells in the concentrated population may be about $0.5 \times 10^6$; about $0.75 \times 10^6$; about $1 \times 10^6$; about $1.25 \times 10^6$; about $1.5 \times 10^6$; about $1.75 \times 10^6$; about $2 \times 10^6$; about $2.25 \times 10^6$; about $2.5 \times 10^6$; about $2.75 \times 10^6$; or about $3 \times 10^6$ cells/ml of the aqueous medium. In a particular embodiment, the density of the CHO cells in the concentrated population is from about $1 \times 10^6$ to about $2.5 \times 10^6$ cells/ml of the aqueous medium; more preferably in this embodiment from about $1.5 \times 10^6$ to about $2.5 \times 10^6$ cells/ml of the aqueous medium; thus, for example, the density of the CHO cells in the concentrated population may be from about $1.75 \times 10^6$ to about $2.25 \times 10^6$; from about $1.8 \times 10^6$ to about $2.2 \times 10^6$; from about $1.85 \times 10^6$ to about $2.15 \times 10^6$; or from about $1.9 \times 10^6$ to about $2.1 \times 10^6$ cells/ml of the aqueous medium. By way of another example, the density of CHO cells in the concentrated population may be about $1.75 \times 10^6$; about $2 \times 10^6$; or about $2.25 \times 10^6$ cells/ml of the aqueous medium. It will be understood that the density of CHO cells prior to concentration and the density of the CHO cells after concentration may be anywhere within the above ranges, provided that the density after concentration is greater than the density prior to concentration.

In general, the density of a population of CHO cells may be concentrated according to a variety of methods. For example, the cell density may be concentrated by centrifuging or filtering the CHO cells in the population, removing a portion of the aqueous medium, and resuspending the CHO cells in the same or different aqueous medium at the desired concentrated density of CHO cells. Alternatively, the density of the population of CHO cells may be concentrated by removing aqueous media from the suspension culture without removing a substantial number of CHO cells and without replacing the withdrawn media with additional aqueous media (or, in the alternative, replacing the withdrawn media with a lesser volume of additional media) to obtain the desired concentrated density of CHO cells.

Where the CHO cells are not concentrated prior to transfection, the CHO cells are typically transfected at a density of from about $0.5 \times 10^6$ to about $3 \times 10^6$ cells/ml of the aqueous medium. Thus, for example, the density of the population of CHO cells at transfection may be about $0.5 \times 10^6$; about $0.75 \times 10^6$; about $1 \times 10^6$; about $1.25 \times 10^6$; about $1.5 \times 10^6$; about $1.75 \times 10^6$; about $2 \times 10^6$; about $2.25 \times 10^6$; about $2.5 \times 10^6$; about $2.75 \times 10^6$; or about $3 \times 10^6$ cells/ml of the aqueous medium. In a particular embodiment, the density of the population of CHO cells at transfection is from about $0.5 \times 10^6$ to about $1.5 \times 10^6$ cells/ml of the aqueous medium; thus, for example, the density of the population of CHO cells at transfection may be from about $0.75 \times 10^6$ to about $1.25 \times 10^6$; from about $0.8 \times 10^6$ to about $1.2 \times 10^6$; from about $0.85 \times 10^6$ to about $1.15 \times 10^6$; or from about $0.9 \times 10^6$ to about $1.1 \times 10^6$ cells/ml of the aqueous medium. By way of another example, the density of the CHO cells at transfection may be about $0.75 \times 10^6$, about $1 \times 10^6$, or about $1.25 \times 10^6$ cells/ml of the aqueous medium.

Irrespective of the particular stage of growth the population of CHO cells is in, it will be understood that all or substantially all of the cultured CHO cell population may be transfected simultaneously or one or more subpopulations of CHO cells may be transfected separately, provided, however, that the population or subpopulation(s) generally have a cell density within the ranges described herein. Thus, for instance, one or more subpopulations having a density of from about $0.5 \times 10^6$ to about $3 \times 10^6$ cells/ml of the aqueous medium may be separated or withdrawn from a population of CHO cells seeded and cultured to a relatively greater cell density (e.g., greater than $0.5 \times 10^6$, $1 \times 10^6$, $2 \times 10^6$, or $3 \times 10^6$ cells/ml of the aqueous medium) in the log phase of growth (e.g., the early log phase of growth), and transfected in a separate vessel(s). Alternatively, two or more subpopulations of CHO cells seeded and cultured to the log phase of growth may be combined to form a population of CHO cells having a density of from about $0.5\times10^6$ to about $3\times10^6$ cells/ml of the aqueous medium and transfected in a single vessel.

During and/or after the preparation of the CHO cells for transfection as described above, cellular-derived solutes and debris may be present in the aqueous medium. In general, the cellular-derived solutes and debris may include waste products such as negatively charged proteins and/or micro-solutes which can form electrostatic and/or ionic bonds with the polycationic composition comprising linear polyethyleneimine used to deliver nucleic acid to the CHO cells during transfection, inhibiting nucleic acid transfer into the cells and reducing transfection efficiency. The cellular-derived solutes and debris can also generally inhibit the growth and proliferation of the CHO cells before and after transfection.

The concentration of the cellular-derived solutes and debris in the cell culture system may be reduced prior to transfection of the CHO cells (i.e., prior to contacting the CHO cells with the transfection composition comprising linear polyethyleneimine and nucleic acid), or after the transfection of the CHO cells (i.e., after contacting the CHO cells with the transfection composition comprising linear polyethyleneimine and nucleic acid). Preferably, the concentration of the cellular-derived solutes and debris in the cell culture system is reduced prior to transfection of the CHO cells. In general, the concentration of the cellular-derived solutes and debris may be reduced by separating the conditioned media containing the cellular-derived solutes and debris from the cell culture system (e.g., by withdrawing it from the culture vessel) and replacing it with a different aqueous medium; for example, a fresh aqueous medium. It has been found that transfection efficiencies and/or polypeptide production levels may be improved by removing the cellular-derived solutes and debris from the system by replacing the conditioned media containing such components with fresh aqueous media. According to the processes described below, at least a 50% reduction in the concentration of cellular-derived solutes and debris may be obtained. For example, at least 60%; at least 75%; at least 90%; at least 95%; at least 99%; at least 99.5%; or at least 99.9% reduction in the concentration of cellular-derived solutes and debris may be obtained.

Typically, at least some fraction of the conditioned media and the undesirable cellular-derived solutes and debris are separated from the cell culture system and replaced with fresh aqueous medium. For instance, at least 10%, at least 20%, at least 30%, at least 40%, at least 50%, at least 60%, at least 70%, at least 80%, at least 90%, at least 95%, or at least 99%, by volume, of the conditioned media may be withdrawn from the culture system and replaced with fresh aqueous medium. Preferably, at least 50%, by volume, of the conditioned aqueous media is separated from the population of CHO cells. Typically, greater than 50%, by volume, of the conditioned media is separated from the population of CHO cells. For example, at least 60%, at least 65%, at least 70%, at least 75%, at least 80%, at least 85%, at least 90%, at least 95%, or at least 99%, by volume, of the conditioned media may be separated from the CHO cells.

As noted above, the conditioned media that is separated or withdrawn from the cell culture system is preferably replaced with a fresh aqueous media. Generally, 99% or more, by volume, of the conditioned media separated from the CHO cells is replaced with fresh aqueous media. Alternatively, however, less than 99%, by volume, of the conditioned media separated from the CHO cells may be replaced with fresh aqueous media; for example, less than 90%, less than 80%, less than 70%, less than 60%, less than 50%, less than 25%, or less than 10% of the conditioned media separated from the CHO cells may be replaced with fresh aqueous media. The amount of fresh aqueous media used to replace the conditioned media may depend, in part, on the desired cell density of the CHO cells at transfection. For instance, if a more concentrated cell density is desired, a lesser volume of fresh aqueous media may be added to the culture system relative to the volume of conditioned media that was removed from the culture system. Regardless of the particular amount of conditioned media separated from the cell culture system and/or the amount of fresh media used to replace the conditioned media, the separation and replacement may occur simultaneously or substantially simultaneously, or the separation may occur first followed by the replacement.

In general, the fresh aqueous medium added to the cell culture system is not significantly different from the conditioned media except with respect to accumulated cellular-derived solutes and debris such as those described above. For example, the fresh aqueous medium may be newly mixed or otherwise unused media. The fresh aqueous media is preferably the same or substantially similar to the aqueous media used in the preparation of the cells for transfection, as described above. Thus, for example, the fresh aqueous media may be substantially free of serum, protein, lysates, hydrolysates, human-, animal-, and plant-derived components, anti-clumping agents and other cell protectants, and combinations thereof, for the reasons discussed above.

For relatively small culture volumes (i.e., the volume of aqueous media the CHO cells are suspended in), the conditioned media (and the cellular-derived solutes and debris included therein) may be removed from the culture system by centrifuging the CHO cells suspended in the aqueous medium once the CHO cells reach the desired density and/or phase of growth (e.g., early log phase) for transfection described above (e.g., less than 50% of the difference between (a) the density of the CHO cells when they enter the log phase of growth and (b) the density of the CHO cells when they exit the log phase of growth). By way of example, the CHO cells may be centrifuged for about 5 minutes at 100×g to pellet the CHO cells. In general, any length of time and speed of centrifugation may be employed provided it does not adversely affect the cells.

After the formation of the cell pellet by centrifugation, the conditioned media may be removed from the pellet (e.g., by decanting) and the CHO cells may be resuspended in fresh aqueous medium at a desired cell density for transfection. For example, after pelleting the CHO cells may be resuspended at a concentrated density (e.g., about $1\times10^6$ to about $3\times10^6$ cells/ml of the aqueous medium) by removing the conditioned media and replacing the conditioned media with a lesser volume of fresh aqueous medium. Alternatively, after pelleting the CHO cells may be resuspended at a substantially similar density to the density they were at prior to removal of the conditioned media (i.e., the cells are not concentrated) by removing the conditioned media and replacing the conditioned media with a substantially equal volume of fresh aqueous media. By way of another alternative, after pelleting the CHO cells may be resuspended at a more dilute cell density by removing the conditioned media and replacing the conditioned media with a greater volume of fresh aqueous media. In one embodiment in which the conditioned media is removed and replaced with a substantially equal volume or a greater volume of fresh aqueous media, the resuspended cell density is about $0.75\times10^6$ to about $1.5\times10^6$ cells/ml of the aqueous medium; more preferably in this embodiment the cells are resuspended at a density of about $1\times10^6$ cells/ml of the aqueous medium. In another embodiment in which the conditioned media is removed and replaced with a lesser volume of fresh aqueous media (i.e., to concentrate the cell density), the resuspended cell density is about $1\times10^6$ to about $3\times10^6$ cells/ml of the aqueous medium; more preferably in this embodiment the cells are resuspended at a density of about $2\times10^6$ cells/ml of the aqueous medium.

As noted above, the density of the population of CHO cells after the separation of the population from the conditioned media and replacement of the conditioned media with fresh media may or may not be similar to the density of the population of CHO cells before the separation and replacement. For example, the density of the population of CHO cells after the separation and replacement may be substantially the same as the density of the population of CHO cells before the separation and replacement; that is, the density of the population of CHO cells after the separation and replacement may be no more than 50% greater or 50% less than the density of the population of cells before the separation and replacement. By way of another example, the density of the population of CHO cells after the separation and replacement may be no more than 40% greater or 40% less, 30% greater or 30% less, 20% greater or 20% less, 10% greater or 10% less, or 5% greater or 5% less than the density of the population of cells before the separation and replacement.

Alternatively, the density of the population of CHO cells after the separation of the population from the conditioned aqueous media and after the replacement of the conditioned aqueous media with fresh aqueous media may be different than the density of the population of CHO cells before the separation and replacement. For example, the density of the population of CHO cells after the separation and replacement may be 50% greater, 75% greater, 90% greater, 99% greater, or about 99.99% greater than the density of the population of CHO cells before the separation and replacement. By way of another example, the density of the population of CHO cells after the separation and replacement may be 50% less, 75% less, 90% less, 99% less, or about 99.99% less than the density of the population of cells before the separation and replacement.

By way of example, the CHO cells may be cultured (e.g., in 30 milliliters of aqueous medium) until they reach the early log phase of growth and/or have a density of about $1\times10^6$ cells/ml of the aqueous medium. The conditioned media may then be removed (e.g., by pelleting and decanting) and the cells resuspended in about half the volume of fresh media (e.g., 15 milliliters), effectively concentrating the cell density to about $2\times10^6$ cells/ml of the aqueous medium. The concentrated population of CHO cells may then be transfected as described below. After transfection, the concentrated population may be diluted with additional aqueous medium to lower the cell density and/or to dilute the concentration of the transfection composition (described in further detail below) (e.g., a 3× dilution, increasing the cell culture volume to about 45 milliliters). It will be understood that a similar protocol could be readily scaled up to considerably larger cell culture volumes, such as in a bioreactor.

By way of another example, the CHO cells may be cultured (e.g., in 45 milliliters of aqueous medium) until they reach the early log phase of growth and/or have a density of about $1\times10^6$ cells/ml of the aqueous medium. The conditioned media may then be removed (e.g., by pelleting and decanting) and the cells resuspended in the same volume of fresh aqueous medium (e.g., 45 milliliters), effectively maintaining the cell density at about $1\times10^6$ cells/ml of the aqueous medium. The population of cells may then be transfected as described below. Since the cells are already at a density that is generally conducive for further growth (i.e., early log phase and/or unconcentrated) they do not necessarily need to be diluted after transfection is complete, provided the amount of linear polyethyleneimine utilized in the transfection composition is not significantly toxic to the cells (described in further detail below). As in the preceding paragraph, a similar protocol could be readily scaled up to considerably larger cell culture volumes, such as in a bioreactor.

The temperature of the aqueous medium used to replace the conditioned media and/or to resuspend the cells at the desired density is preferably the same or similar to the temperature of the conditioned medium that is being withdrawn from the cell culture system. Accordingly, the fresh aqueous media is preferably warmed (e.g., by a waterbath or incubator) prior to resuspending the cells at the desired density.

In general, centrifugation processes for withdrawing the conditioned media (and cellular-derived solutes and debris) from the culture system such as those described above may be employed when the culture volume is from about 1 milliliter to about 20,000 milliliters; more preferably from about 15 milliliters to about 13,000 milliliters.

For larger culture volumes such as, for instance, CHO cells cultured in a bioreactor, the concentration of cellular-derived solutes and debris may be reduced by diafiltration methods. In general, diafiltration utilizes microfiltration membranes and techniques to separate the conditioned media from the cell culture system and the CHO cells, removing or lowering the concentration of cellular-derived solutes and debris in the cell culture system overall. The microfiltration membrane retains the cells in the system, but allows the conditioned medium and the smaller solutes and debris to leave the system. The diafiltration process employs permeable, semi-permeable, or porous membranes to separate the components in the culture suspension based on their molecular size. Generally, the diafiltration process involves pumping the conditioned media out of the cell culture system and with it the cellular-derived solutes and debris. Using diafiltration, at least a fraction of the population of CHO cells are preferably maintained in suspension in the aqueous medium during the withdrawal of the conditioned media and/or the cellular-derived solutes and debris contained therein, in contrast to the centrifugation methods described above. In general, diafiltration processes for withdrawing the conditioned media (and cellular-derived solutes and debris) from the culture system such as those described herein may be employed when the culture volume is from about 10 liters to about 100,000 liters; more preferably from about 20 liters to about 20,000 liters.

Where the density of the population of CHO cells is concentrated prior to transfection (e.g., to a density of from about $1\times10^6$ to about $3\times10^6$ cells/ml of the aqueous medium), the concentration step may be performed prior to performing the diafiltration process, after performing the diafiltration process, or during the diafiltration process. For instance, the concentration may be performed by pumping the conditioned medium through the microfiltration membrane and out of the cell culture system (e.g., out of the bioreactor) without simultaneously or subsequently adding fresh media back into the cell culture system. Alternatively, a fraction of the conditioned media may be removed from the cell culture system and fresh aqueous medium may be simultaneously or subsequently added back into the cell culture system but at a lesser volume than the volume of conditioned media withdrawn from the system as described above. Advantageously, concentrating the cells in suspension prior to or during diafiltration also enables the use of smaller volumes of fresh aqueous medium to be employed during the diafiltration processes described below. Concentrating the cells in this manner also results in the removal of at least a percentage of undesirable cellular-derived solutes and debris from the system.

The microfiltration system and membrane for performing the diafiltration may be attached to a bioreactor such as those described below. Typically, the microfiltration membrane has a pore size of from about 0.2 µm. Generally, CHO cells have a diameter of about 10-15 µm; thus, they will not pass through the microfilter. Typically, the microfiltration membrane has a surface area of about 500 cm$^2$ to about 4×10$^6$ cm$^2$. One example of a microfiltration membrane that may be used is commercially available from GE Healthcare (Product No. CFP-2-E-6A, Piscataway, N.J.), and has a pore size of about 0.2 µm and a surface area of about 2800 cm$^2$.

The diafiltration process is preferably a continuous diafiltration (i.e., a constant volume diafiltration). In general, continuous or constant volume diafiltration involves removing the cellular-derived solutes and debris in the conditioned media by adding fresh aqueous media to the culture system at about the same rate that the conditioned media is being withdrawn or removed from the culture system. Thus, the culture volume retained in the system (i.e., the retentate), cell culture media component concentration, and cell density does not substantially change during the continuous diafiltration process. The amount of cellular-derived solutes and debris removed from the cell culture system is generally related to the volume of media filtrate generated relative to the volume of media retained in the system, as described below.

The volume of media withdrawn or removed from the system (i.e., the filtrate) may be referred to in terms of diafiltration volume; that is, a single diafiltration volume is the cell culture volume at the beginning of diafiltration. As previously noted, in a continuous diafiltration fresh aqueous media is added to the system at about the same rate as filtrate aqueous media (i.e., conditioned media) is being withdrawn or removed from the system. When the amount of filtrate removed from the system is substantially equal to the culture volume at the start of diafiltration, one diafiltration volume has been removed from the system.

Efficiency of removal of cellular-derived solutes and debris from the system according to continuous (i.e., constant volume) diafiltration may be generally described according to the following formula:

$$\ln(C_O/C) = (V_W)/(V_O)$$

wherein $C_O$ is the initial concentration of cellular-derived solutes and debris; C is the concentration of cellular-derived solutes and debris after diafiltration; $V_W$ is the volume of fresh aqueous medium added to the system while withdrawing a substantially equal volume of conditioned cell culture media containing the cellular-derived solutes and debris from the system, minus the holdup volume of the filtration system to the exit port (also referred to as the extra-capillary space) of the microfilter; and $V_O$ is the average culture volume of the sample being filtered (e.g., the concentrated or unconcentrated volume of media in which the CHO cells are suspended). See, e.g., Munir Cheryan, Ultrafiltration Handbook, Technomic Pub. Co. (1986).

By way of example, Table 1 illustrates the percent removal of undesirable cellular-derived solutes and debris that may be obtained according to the above formula and the continuous (i.e., constant volume) diafiltration process described above; that is, by adding fresh aqueous medium to the system while removing conditioned media.

TABLE 1

| $V_w/V_o$ | Removal of cellular-derived solutes and debris |
|---|---|
| 1 | 63.2 |
| 2 | 86.5 |
| 3 | 95.0 |
| 4 | 98.2 |
| 5 | 99.3 |
| 10 | 99.9985 |

Thus, $V_W/V_O$ in Table 1 generally corresponds to diafiltration volume as described above.

Alternatively, a variety of other diafiltration processes may be employed to remove the undesirable cellular-derived solutes and debris from the aqueous medium through the withdrawal of the conditioned media from the cell culture system and the replacement of the conditioned media with fresh media. For example, the diafiltration process may involve discontinuous diafiltration by sequential dilution. In general, this process involves diluting the cell culture with fresh aqueous medium to a predetermined increased volume (e.g., a 2×, 3×, 4×, . . . etc. increase relative to the original concentrated or unconcentrated volume). Typically, the culture is diluted with an equal volume of fresh aqueous medium (i.e., a 2× dilution). The volume of the diluted sample is then decreased back to the initial volume by diafiltration (i.e., by the withdrawal of the conditioned media from the cell culture system) and the process is repeated until the desired reduced concentration of cellular-derived solutes and debris is achieved. Each subsequent dilution and volume reduction step removes additional solutes and debris (e.g., 1 diafiltration volume results in a 50% reduction of the concentration of cellular-derived solutes and debris in the culture system; 2 diafiltration volumes result in a 75% reduction of the concentration of cellular-derived solutes and debris in the culture system; 3 diafiltration volumes result in a 88% reduction of the concentration of cellular-derived solutes and debris in the culture system; 4 diafiltration volumes result in a 94% reduction of the concentration of cellular-derived solutes and debris in the culture system; and so on).

By way of an alternative example, discontinuous diafiltration using volume reduction may be employed. This process generally reverses the process described above in connection with discontinuous diafiltration by sequential dilution. That is, the cell culture volume is concentrated to a predetermined reduced volume (e.g., a 2×, 3×, 4×, . . . etc. decrease relative to the original concentrated or unconcentrated volume) through the withdrawal of conditioned media from the cell culture system, followed by diluting the cell culture volume back to its original volume. As with sequential dilution discontinuous diafiltration, the process may be repeated until the desired reduced concentration of cellular-derived solutes and debris is achieved, and each subsequent concentration and dilution step removes additional solutes and debris.

Regardless of the particular diafiltration method employed, before, during, or after diafiltration the density of the CHO cells may be adjusted to any desired cell density (e.g., by adjusting the amount of media added to and/or removed from the cell culture system).

Transfection of the CHO Cells

Once the CHO cells are prepared for transfection, the cells are combined with a transfection composition for delivering nucleic acid to the cells. The transfection composition contains nucleic acid and a polycationic composition comprising linear polyethyleneimine. The transfection composition is typically delivered to the CHO cells in the form of an aqueous transfection reagent containing an aqueous medium and a population of particles dispersed in the aqueous medium. As noted above, the particles (or at least a fraction thereof) include nucleic acid and the polycationic composition comprising linear polyethyleneimine. Preferably, the aqueous transfection reagent has a pH of about 7.0 to about 7.6; more preferably about 7.1 to about 7.4.

Where the transfection composition is delivered to the CHO cells in the form of an aqueous transfection reagent, the volume of aqueous medium in the transfection reagent is typically about 1% to about 15% of the culture volume at transfection (i.e., the total volume of aqueous medium in which the CHO cells are suspended in at the time of transfection); preferably about 5% to about 15%. In a particular embodiment, the volume of aqueous medium in the transfection reagent is from about 6% to about 10% of the culture volume at transfection. For example, if the culture volume at transfection is about 4 liters of aqueous media, then about 400 milliliters (~10%) of the aqueous transfection reagent containing the transfection composition and an aqueous medium may be combined with the CHO cells in culture. By way of another example, if the culture volume at transfection is about 12 liters of aqueous media, then about 720 milliliters (~6%) of the aqueous transfection reagent containing the transfection composition and an aqueous medium may be combined with the CHO cells in culture.

In general, the CHO cells and the transfection composition (e.g., the aqueous transfection reagent containing an aqueous medium and the transfection composition) are combined by mixing or dispersion in a vessel. For example, the transfection composition may be dispersed in the cell culture vessel in which the CHO cells are cultured. Alternatively, the CHO cells may be dispersed in a vessel containing the transfection composition. In another alternative example, the CHO cells and the transfection composition may be dispersed in a separate vessel initially lacking both the CHO cells and the transfection composition. In a particular embodiment, the transfection composition is combined with CHO cells cultured in a bioreactor. Regardless of how the CHO cells and the transfection composition are combined, the combination is preferably agitated (e.g., by stirring) to maximize the exposure of the CHO cells to the transfection composition.

After the transfection composition and the CHO cells are combined, the combination is incubated. The combination of the CHO cells and the transfection composition is typically incubated for about 3 hours to about 6 hours. Accordingly, for example, the mixture may be incubated for at least about 3 hours; at least about 3.5 hours; at least about 4 hours; at least about 4.5 hours; at least about 5 hours; at least about 5.5 hours; or at least about 6 hours. Preferably, the mixture is incubated for about 4 hours. It is contemplated that longer or shorter incubation times may also be employed; shorter incubation times, however, generally result in lower transfection efficiencies, while longer incubation times may adversely affect cell viability, as the transfection composition can be toxic to the CHO cells. During incubation, CHO cells take up (i.e., endocytose) the nucleic acid in the population of particles, forming transfected CHO cells. Successful formation of transfected CHO cells is generally recognized when any indication of the operation of the nucleic acid occurs within the CHO cell.

Conditions during the incubation of the combination of the CHO cells and the transfection composition are generally the same as those described above for the preparation of the CHO cells for transfection (e.g., 37° C., 5-8% $CO_2$, 60% dissolved $O_2$). However, any incubation condition that combines with the other parameters described herein to produce the desired transfection efficiency and/or level of polypeptide production is contemplated for use in the processes of the present invention.

Following incubation, the combination of the CHO cells and the transfection composition may be diluted with an aqueous medium. The combination is generally diluted to attenuate the concentration of the transfection composition to a level that is not significantly toxic to the transfected CHO cells. If, however, a sufficiently low concentration of nucleic acid is used in the transfection composition (e.g., about 0.5 to about 2.0 µg/ml), which corresponds to a lower concentration of linear polyethyleneimine (i.e., according to the N/P ratio described below), dilution may not be necessary. Thus, for example, the culture volume during initial culture, growth to log phase, transfection, and post-transfection culture can remain substantially the same throughout the process. Additionally or alternatively, where the density of CHO cells was concentrated prior to transfection, for example, the dilution step can serve to dilute the density of CHO cells to a density more conducive to the growth and proliferation of the transfected CHO cells. Further, this can maximize the length of time that the transfected CHO cells can express polypeptides encoded by the nucleic acid.

Where the CHO cells were concentrated prior to transfection, the transfected CHO cells are preferably diluted from the concentrated density to a cell density more commonly associated with the early- to mid log phase of growth. Typically, the density of transfected CHO cells is diluted by a factor of about 1.5× to about 4×; preferably, about 3×. For example, the transfected CHO cells may be diluted from a concentrated cell density of from about $0.5 \times 10^6$ to about $3 \times 10^6$ cells/ml of aqueous medium to a more dilute cell density of about $6.6 \times 10^5$ to about $2 \times 10^6$; from about $5 \times 10^5$ to about $1.5 \times 10^6$; from about $4 \times 10^5$ to about $1.2 \times 10^6$; from about $3.3 \times 10^5$ to about $1 \times 10^6$; from about $2.9 \times 10^5$ to about $8.6 \times 10^5$; or from about $2.5 \times 10^5$ to about $7.5 \times 10^5$ cells/ml of aqueous medium. By way of another example, the transfected CHO cells may be diluted from a concentrated density to a more dilute density of about $2.6 \times 10^5$; about $3.6 \times 10^5$; about $4.6 \times 10^5$; about $5.6 \times 10^5$; about $6.6 \times 10^5$; about $7.6 \times 10^5$; or about $8.6 \times 10^5$ cells/ml of aqueous medium. It will be understood that the density of the CHO cells prior to dilution and the density of the CHO cells after dilution may be anywhere within the above ranges, provided that the density after dilution is less than the density prior to dilution.

As noted above, the combination may be diluted with an aqueous medium. The aqueous medium used to dilute the combination is generally the same or substantially similar to the aqueous suspension medium used in the preparation of the CHO cells for transfection. For example, the aqueous medium used to dilute the combination is preferably substantially free of serum, protein, lysates, hydrolysates, human-, animal-, and plant-derived components, anti-clumping agents and other cell protectants, and combinations thereof, for the reasons discussed above.

Following transfection, it may be desirable to include nutrients (e.g., L-glutamine, glucose, and the like), anti-clumping agents (e.g., dextran sulfate), and/or other cell protectants (e.g., Pluronic® F-68) to the aqueous medium. Such components are typically added to the aqueous medium about 24-48 hours after transfection. Adding these components too soon after transfection may tend to lower transfection efficiencies and/or polypeptide production; allowing the cells to remain in culture too long without such components, however, may adversely affect cell viability. In general, anti-clumping agents may be included in the aqueous medium following transfection at a concentration of about 1 milliliter to about 4 milliliters per liter of culture volume using a 1000× stock solution. Cell protectants such as Pluronic® F-68 may be included in the aqueous medium following transfection at a concentration of up to about 0.1% (w/v). Various nutrients may also be added to the system following transfection (e.g., as in a fed-batch system) at concentrations that generally support the continued growth and viability of the transfected CHO cells.

Once the CHO cells are transfected and, if desired, diluted with additional aqueous media to a more dilute cell density, they are generally maintained in suspension culture in the aqueous medium. During this post-transfection incubation period, the transfected CHO cells grow and proliferate, and the particular nucleic acid that has been transfected functions, i.e., is transcribed and translated, to produce the desired polypeptide. Over the course of the post-transfection culture, the polypeptide(s) produced and/or expressed by the transfected CHO cells may be analyzed and/or recovered.

The post-transfection culture techniques and conditions (e.g., agitation, temperature, pH, humidity, $CO_2$ level, dissolved $O_2$ level, and the like) are generally the same or similar to the culture conditions employed in the preparation of the CHO cells for transfection and/or the culture conditions employed during transfection. It is contemplated, however, that any one or more of the above-described culture conditions may be adjusted as needed to account for any differences between the CHO cells in culture before and after transfection.

The transfection of CHO cells according to the various processes and embodiments described herein may improve transfection efficiencies and/or polypeptide production relative to conventional methods. For example, CHO cells can be transfected according to the processes described herein at transfection efficiencies of greater than 70%; preferably greater than 80%; more preferably greater than 90%; still more preferably greater than 95%; and still more preferably greater than 99% (e.g., 99.9%). One method of measuring transfection efficiency is by quantifying the expression of a reporter gene that has been transfected into the cell as part of the transfection composition, for example, by fluorescent or functional quantification assays (see Examples). Suitable reporter genes and methods for quantifying their expression in a transfected CHO cell are generally known in the art and described in further detail below.

As noted above, polypeptide production may also be improved relative to conventional transfection methods. The particular amount(s) of polypeptide produced by CHO cells transfected according to the processes and compositions described herein can vary considerably depending on the particular CHO cell line employed, the particular nucleic acid(s) delivered to the cells, and/or the polypeptide(s) encoded by said nucleic acids. In general, polypeptides may be produced or otherwise expressed by CHO cells on the order of tens, hundreds, or even thousands of milligrams per milliliter.

Transfection of CHO Cells in a Bioreactor

As noted above, in one embodiment the CHO cells are prepared, transfected, and maintained in culture post-transfection in a bioreactor. In general, the CHO cells may be cultured in a bioreactor according to a batch or fed-batch system, as described above. Preferably, the CHO cells are cultured in a bioreactor according to a fed-batch system. Conventional bioreactors may be utilized in the processes of the present invention, and their use in the culture and transfection of cells is well known in the art.

Bioreactors typically consist of a cell culture vessel and a headplate coupled to the vessel to form a sealed reservoir for holding the cells and the aqueous medium in which they are cultured. The vessel is commonly glass or plastic, and the headplate is commonly metal (e.g., stainless steel), glass, or plastic. The vessel is generally jacketed with heating and cooling means for controlling the temperature of the cell culture.

The total volume of the bioreactor can vary considerably depending on the size of the vessel employed. In general, the present invention may be used to transfect CHO cells in bioreactors of any size. Conventional bioreactors, for example, typically have capacities of a fraction of a liter to about 20,000 liters, or higher. In a particular embodiment, the bioreactor has a total volume of about 12 liters to about 14 liters.

The reservoir typically includes some amount of vapor-space between the top surface of the cell culture medium and the bottom of the headplate. On a percentage basis, the vapor-space will typically comprise about 10% to about 40% of the total bioreactor volume; in a particular embodiment, the vapor-space comprises about 10% to about 20% of the total bioreactor volume. The vapor space typically includes a gas such as $CO_2$, $N_2$, and/or $O_2$, and may be optionally used for controlling dissolved oxygen for the cells.

One or more ports or inlets are typically positioned on the vessel and/or the headplate for the addition of various components into the sealed reservoir (e.g., into the cell culture media system and/or the vapor-space). For example, the bioreactor commonly includes at least one addition port for introducing aqueous media (e.g., fresh aqueous media) and components thereof (e.g., nutrients such as monosaccharides and/or amino acids), cells, transfection compositions, and the like, to the sealed reservoir. The ports or inlets may be connected to feed lines and/or pumps for the automated introduction of such components. Such addition ports may be utilized in connection with, for instance, a fed-batch culture system.

The bioreactor also typically includes one or more outlets for the removal or release of components contained in the sealed reservoir. For example, the bioreactor may include one or more harvest outlets for removing the cell culture media and/or cells from the reservoir (e.g., for polypeptide recovery). By way of another example, the bioreactor may include a sampling outlet for the aseptic removal or components (e.g., cells, culture media) from the reservoir (e.g., for determining cell density or quantifying the polypeptide produced by the transfected cells). The bioreactor may additionally include one or more exhaust filters for the release of gases from the sealed reservoir. The outlets may also be used to remove or withdraw conditioned aqueous media from a reservoir equipped with a filtration system such as, for instance, those described above in connection with diafiltration processes.

In operation, the various components in the sealed reservoir (e.g., cells, cell culture media system, transfection composition) are typically continuously or substantially continuously agitated in the sealed reservoir using an impeller (e.g., a marine- or pitched blade impeller). The impeller is preferably operated at relatively low shear (e.g., 15-20 rpm) so as not to harm the cells. In general, however, any impeller speed may be employed provided the cell viability is not substantially compromised.

The bioreactor also typically includes various sensors, such as temperature sensors, pH sensors, oxygen sensors, and the like, for respectively measuring the levels of such conditions in the bioreactor. Additionally, these sensors may be connected to a preprogrammable microprocessor. The microprocessor may be further connected to pumps for adding certain reactants to the sealed reservoir for adjusting the cell culture conditions and/or cell culture reagents.

A suitable bioreactor for use in the present invention is the CelliGen Plus® stirred-tank bioreactor, New Brunswick Scientific Co., Edison, N.J. Alternatively, a substantially equivalent bioreactor system may be employed.

Preparation of Polypeptides from Transfected CHO Cells

Another aspect of the present invention is directed to processes for the production of a polypeptide from transfected CHO cells. The transfection process, in general, may be used to insert nucleic acid encoding for a polypeptide into the CHO cells. Following transfection, the CHO cells transcribe and translate the nucleic acid to produce the polypeptide, at least transiently, and the polypeptide may be recovered.

As noted above, the cell culture components and nutrients can generally only be limitedly renewed by supplementation (e.g., as in a fed-batch system), therefore exponential growth of the CHO cells post-transfection is typically limited to a few generations (e.g., about 6 generations). Eventually, waste products from the transfected CHO cells will accumulate in the aqueous medium, the CHO cells will reach a maximum density, and/or the CHO cells will exhaust all of the available nutrients in the aqueous medium, and the cells will typically exit the log phase of growth and enter the stationary phase. In the stationary phase, the rate of cell division is substantially balanced by the rate of cell death. As the cells begin to decline in viability and/or die, they may begin to release undesirable cellular components. Thus, it is generally desirable to recover the polypeptide from the aqueous medium and/or from the transfected CHO cells prior to the CHO cells entering into the death phase (i.e., the phase in which the cells begin to die off with little or no additional cell division), as the polypeptide produced by the cells at this point may be of lower quality and/or the cellular components and factors released by the cells may adversely affect quality, recovery, and/or purification of the polypeptide.

The transfected CHO cells are typically maintained in culture for about 5 to about 14 days before recovering the polypeptide. For example, the transfected CHO cells may be maintained in culture for about 5 days; about 6 days; about 7 days; about 8 days; about 9 days; about 10 days; about 11 days; about 12 days; about 13 days; or about 14 days; before recovering the polypeptide. The length of time that the transfected CHO cells are cultured prior to recovering the polypeptide can depend on a variety of factors such as, for example, the particular CHO cell line which was transfected, the particular polypeptide being expressed, the aqueous medium in which the CHO cells are cultured, the culture conditions, the supplemental addition of nutrients, anti-clumping agents, and/or cell protectants, and/or a number of other factors; longer or shorter periods of time, therefore, are also contemplated.

The polypeptide may be produced by the transfected CHO cells as an insoluble aggregate or as a soluble peptide in the periplasmic space or cytoplasm of the cell, or in the extracellular medium (i.e., secreted into the aqueous medium). Thus, the polypeptide may be recovered from either one of the aqueous medium or the transfected CHO cells, or both. In a particular embodiment, the polypeptide is recovered from the aqueous medium. The transfected CHO cells and the aqueous medium are preferably separated (e.g., by filtration or centrifugation) prior to recovery. Where the polypeptide is stored in the cells, for example, the cells are typically collected and disrupted in order to recover the polypeptide. Where the polypeptide is secreted into the aqueous media by the transfected CHO cells, for example, the cells are typically separated from the aqueous media by centrifugation prior to recovering the polypeptide from the aqueous media. The polypeptide may also be purified during or after recovery.

Various techniques suitable for use in chemical, biomolecular, and biological recovery, quantification, and/or purification of polypeptides are well known to those of skill in the art and include, for example, precipitation with ammonium sulfate, polyethylene glycol, antibodies and the like or by heat denaturation, followed by centrifugation; fractionation, chromatographic procedures, including but not limited to, partition chromatography (e.g., paper chromatography, thin-layer chromatography (TLC), gas-liquid chromatography and gel chromatography), gas chromatography, high performance liquid chromatography, affinity chromatography (e.g., using bacterial proteins that bind to immunoglobulins and/or antibody-antigen complexes by immuno or non-immuno mechanisms, such as Protein A or Protein G), supercritical flow chromatography, ion exchange, gel filtration, reverse phase, hydroxylapatite, lectin affinity; isoelectric focusing and gel electrophoresis; and immuno-detection methods such as enzyme-linked immunosorbent assay (ELISA) (see, e.g., Sambrook et al. (2001), supra; and Freifelder, Physical Biochemistry, Second Edition, pages 238-246).

In general, the polypeptide may be homologous to the CHO cells (i.e., endogenous to CHO cells), or the polypeptide may be heterologous to the CHO cells (i.e., foreign to the CHO cells). Preferred polypeptides are eukaryotic, and more preferably mammalian.

The polypeptide encoded by the nucleic acid delivered to the CHO cells may be any polypeptide capable of being expressed in CHO cells. Exemplary mammalian polypeptides which may be produced and recovered according to the transfection processes described herein include, for example, renin, a growth hormone, including human growth hormone; bovine growth hormone; growth hormone releasing factor; parathyroid hormone; thyroid stimulating hormone; lipoproteins; cxl-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA) including variants thereof such as glycosylation variants, e.g., TNK; bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-$\beta$; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin (EPO); osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides. In one embodiment, the polypeptide is an antibody. In general, any antibody which may be expressed by transfected CHO cells may be produced, recovered, and/or purified according to the processes of the present invention. For example, the polypeptide may be a monoclonal antibody or an Fc-fusion antibody.

Transfection Compositions

In general, the transfection composition contains a polycationic composition and nucleic acid. The transfection composition typically has an effective average diameter and a polydispersity about this average of less than 0.4. For instance, the transfection composition may have an effective average diameter of about 425 to about 500 nm, about 480 to about 700 nm, or about 350 to about 850 nm and a polydispersity about this average of less than 0.4. Additional and/or alternative characteristics of the transfection composition are described in further detail below.

Polycationic Composition

The vehicle used to deliver nucleic acid to the CHO cells according to the transfection processes of the present invention comprises a polycationic composition. The polycationic composition may be a single composition or a mixture of two or more compositions. The polycationic composition preferably comprises linear polyethyleneimine. More preferably, the polycationic composition predominantly comprises linear polyethyleneimine. For example, the polycationic composition may comprise greater than about 50% linear polyethyleneimine; greater than about 75% linear polyethyleneimine; greater than about 90% linear polyethyleneimine; greater than about 95% linear polyethyleneimine; or greater than about 99% linear polyethyleneimine. In general, linear polyethyleneimine, in contrast to the branched isoform, provides superior results in the transfection composition and the processes of the present invention.

Linear polyethyleneimine is commercially available in a wide range of molecular weights. Generally, the upper limit of the molecular weight of the linear polyethyleneimine is determined by the solubility of the linear polyethyleneimine and/or the toxicity of the linear polyethyleneimine to the CHO cells. Accordingly, the linear polyethyleneimine will typically have a molecular weight of less than about 800 kDa. For example, the linear polyethyleneimine may have a molecular weight of less than about 250 kDa; less than about 100 kDa; less than about 75 kDa; less than about 30 kDa; less than about 15 kDa; or less than about 5 kDa. In a particular embodiment, the linear polyethyleneimine has a molecular weight of about 25 kDa.

Linear polyethyleneimine formulations are also available in a wide range of purity levels. Conventional methods of synthesizing linear polyethyleneimine of varying molecular weight involve the acid hydrolysis of poly(2-ethyl-2-oxazoline). As such, this compound is commonly present as an impurity in the linear polyethyleneimine formulation, typically in the range of 5%-15%. Preferably, the linear polyethyleneimine utilized in the transfection composition has a known purity level. Linear polyethyleneimine of known purity can be obtained commercially, for instance, from Polysciences, Inc., Warrington, Pa. Linear polyethyleneimine is a solid at room temperature, and is preferably prepared for storage and use in a stock solution (e.g., 1 to 100 mg/ml) by dilution in, for example, water, RNase/DNase-free water, buffer solution, alcohols such as ethanol, and the like. In general, dilution of the linear polyethyleneimine in alcohols such as ethanol is preferred, as hydroxy ions from water can undesirably react with the amino moieties of the linear polyethyleneimine. Accordingly, alcohols which are substantially water-free (e.g., anhydrous ethanol) are generally preferred. Typically, the stock solution is separated into aliquots and stored at 4° C. or below.

Nucleic Acid

As noted above, the nucleic acid delivered to the CHO cells by the transfection composition will generally encode a desired polypeptide. The nucleic acid may be made by various techniques known to those of skill in the art such as, for example, chemical synthesis or recombinant production. The nucleic acid is also typically purified. Various methods of purifying nucleic acids such as DNA, RNA, and derivatives and analogs thereof are known in the art and include, for example, alkaline lysis, purification on polyacrylamide gels, cesium chloride centrifugation gradients, differential precipitation, ion-exchange chromatography, gel filtration, combinations thereof, and the like. See, e.g., Sambrook et al. (2001), supra. Preferably, the nucleic acid is substantially free of endotoxins. One method of measuring the purity of a nucleic acid sample is by determining the ratio of spectrophotometric absorbance of the sample at 260 nm to that of 280 nm (i.e., the $A_{260}/A_{280}$ ratio). Preferably, the nucleic acid has an $A_{260}/A_{280}$ ratio of at least 1.5; more preferably at least 1.6; more preferably at least 1.7; most preferably at least 1.8. It is known in the art, however, that the pH and/or ionic strength of aqueous solutions used to dilute nucleic acids for spectrophotometric analysis can affect the $A_{260}/A_{280}$ ratio, therefore ratios outside of these ranges are also contemplated.

The nucleic acid may be a portion of a vector. As used herein, the term "vector" refers to a carrier nucleic acid molecule into which a nucleic acid sequence may be inserted for introduction into a cell where it can be replicated. Vectors include, for example, plasmids, cosmids, viruses (e.g., phages and plant and animal viruses), and artificial chromosomes (e.g., yeast artificial chromosomes (YACs) and bacterial artificial chromosomes (BACs)).

The nucleic acid is preferably included in an expression vector. As used herein, the term "expression vector" refers to nucleic acid sequences containing a desired coding sequence and appropriate nucleic acid sequences necessary for the expression of the operably linked coding sequence in a particular host organism. Expression vectors often contain an expression cassette including a promoter (described below), cloning sites immediately 3' (downstream) of the promoter, and transcription termination signals, and may also include other coding sequences that serve functions other than transcription and translation. In a particular embodiment, the expression vector is a mammalian expression vector. Suitable mammalian expression vectors for use in the expression of polypeptides in mammalian cells are well known in the art, and are commercially available from, for instance, Promega (Madison, Wis.), Stratagene (La Jolla, Calif.), and Clontech (Mountain View, Calif.).

Promoters are control sequences that bind RNA polymerase in a cell to initiate transcription of the 3' (downstream) operably linked coding sequence. The promoter may or may not be used in conjunction with an "enhancer," which is a cis-acting (or in some cases trans-acting) control sequence involved in the efficient transcription of cellular genes and generally functions in an orientation- and position-independent manner. Promoters which may be used in the present disclosure may be inducible, constitutive, and/or generally suitable under appropriate conditions to direct high level expression of the introduced nucleic acid portion, as desired in the production of recombinant polypeptides. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like. In a particular embodiment, the promoter is a cytomegalovirus (CMV) promoter.

The expression vector may optionally include a reporter (i.e., marker) gene sequence. Standard recombinant methods may be used to join the control and/or coding sequences to a reporter gene carried in an expression vector. As noted above, the use of reporter gene sequences is particularly useful in determining the efficiency of the transfection processes described herein. For example, once the CHO cells have been transfected according to the above-described processes, the efficiency of expression of the reporter gene sequence by the transfected CHO cells may be determined by measurement of the reporter mRNA or the reporter polypeptide (e.g., using flow cytometry or other fluorescence detection method), or, in some cases, by enzymatic activity. The type of detection method generally depends on the particular reporter gene sequence utilized. Suitable reporter gene sequences which may be included in the expression vector include, for example, those that encode for chloramphenicol acetyltransferase (CAT), luciferase, β-galactosidase, green fluorescent protein (GFP), their derivatives and/or genetic variants, and the like.

Those of skill in the art will generally know the use of nucleic acids, vectors, expression vectors, promoters, enhancers, reporter genes, and the like, and combinations thereof, for polypeptide expression in cells. (See, e.g., Sambrook et al. (2001), supra).

Characteristics of the Transfection Compositions

When combined (e.g., dispersed in an aqueous medium), the polycationic composition comprising linear polyethyleneimine and the negatively charged nucleic acid described above interact (e.g., non-covalently) to form a transfection composition comprising a population of particles or complexes. More specifically, the polycationic composition comprising linear polyethyleneimine condenses the nucleic acid into a population of smaller particles or complexes comprising nucleic acid and the polycationic composition comprising linear polyethyleneimine. The interaction of the polycationic composition and nucleic acid may include, for example, non-covalent interactions such as hydrogen bonding, ionic bonding, Van der Waals forces, hydrophobic interactions, and the like. In general, the population of particles or complexes formed by the interaction of the nucleic acid and the polycationic composition comprising linear polyethyleneimine are used to deliver the nucleic acid to the CHO cells during transfection. This may be performed by, for example, delivering an aqueous transfection reagent containing an aqueous medium and the transfection composition to the CHO cells as described above.

Particular characteristics of the transfection composition that are generally relevant in the present invention include, for example, the effective average diameter of the transfection composition (i.e., the average particle size) and the polydispersity about this average.

The particles formed by the interaction of the nucleic acid and the polycationic composition comprising linear polyethyleneimine are generally of a polydisperse nature, i.e., the particles in a particular population may vary in size. The effective average diameter of a population of particles, also referred to as the particle size, is generally a measure of the average diameter (or size) of the population of particles. The polydispersity of a population of particles is generally a measure of the width of the particle size distribution. In general, as the polydispersity of a population of particles approaches zero, the particles may be considered to have a substantially uniform diameter or size. See, e.g., Dobrynin et al., Macromolecules (1997), 30, 4756-4765.

The transfection composition typically has an effective average diameter of about 300 to about 1200 nm. Thus, for example, the transfection composition may have an effective average diameter of about 425 to about 1200 nm. Alternatively, the transfection composition may have an effective average diameter of about 300 to about 900 nm. For example, the transfection composition may have an effective average diameter of about 500 to about 850 nm. By way of another example, the transfection composition may have an effective average diameter of about 700 to about 800 nm. By way of another example, the transfection composition may have an effective average diameter of about 400 to about 750 nm.

In one embodiment, the transfection composition has an effective average diameter of about 425 to about 500 nm. Accordingly, for example, the transfection composition may have an effective average diameter of about 430 nm; about 435 nm; about 440 nm; about 445 nm; about 450 nm; about 455 nm; about 460 nm; about 465 nm; about 470 nm; about 475 nm; about 480 nm; about 485 nm; about 490 nm; or about 495 nm. In a particular embodiment, the transfection composition has an effective average diameter of about 450 nm.

In another embodiment, the transfection composition has an effective average diameter of about 350 to about 850 nm. Accordingly, for example, the transfection composition may have an effective average diameter of about 375 nm; about 400 nm; about 425 nm; about 500 nm; about 525 nm; about 550 nm; about 575 nm; about 600 nm; about 625 nm; about 650 nm; about 675 nm; about 700 nm; about 725 nm; about 750 nm; about 775 nm; about 800 nm; or about 825 nm.

In yet another embodiment, the transfection composition has an effective average diameter of about 480 to about 700 nm. Accordingly, for example, the transfection composition may have an effective average diameter of about 520 nm; about 540 nm; about 560 nm; about 580 nm; about 620 nm; about 640 nm; about 660 nm; or about 680 nm. In another particular embodiment, the transfection composition has an effective average diameter of about 570 to about 590 nm.

The transfection composition also preferably has a polydispersity of less than 0.4. Accordingly, for example, the transfection composition may have a polydispersity of less than 0.375, less than 0.35, or less than 0.325. In a particular embodiment, the transfection composition has a polydispersity of less than 0.3. In general, polydispersity may be calculated using a Schultz-Zimm distribution. The calculation of the polydispersity of a population of particles using the Schultz-Zimm formula and distribution is known to those of skill in the art. See, e.g., Dobrynin et al. (1997), supra; Hayter, J. R., Physics of Amphiphiles: Micelles, Vesicles and Microemulsions: Determination of the Structure and Dynamics of Micellular Solutions by Neutron Small-Angle Scattering, DeGiorgio and Corti, eds. (1985), p. 59-93.

It has been found that superior transfection efficiency and/or polypeptide production can be obtained in the transfection processes of the present invention by using a transfection composition having an effective average diameter and/or a polydispersity within the above-described ranges.

Zeta-potential is a measure of the electrostatic potential generated by the accumulation of charges at the surface of a particle or population of particles. This potential, which is measured in milliVolts (mV), may arise by any of several mechanisms including, for example, the dissociation of ionogenic groups in the particle surface and/or the differential adsorption of solution ions into the surface region. In one embodiment, the transfection composition has a zeta-potential of from about 25 mV to about 33 mV; more preferably in this embodiment the zeta-potential is about 29 mV. In another embodiment, the transfection composition has a zeta-potential of from about 18 mV to about 28 mV; more preferably in this embodiment the zeta-potential is from about 19.5 mV to about 26.5 mV.

One method of measuring the effective average diameter (particle size), polydispersity, and/or zeta-potential of the transfection compositions of the present invention is by employing light scattering techniques (e.g., dynamic light scattering, electrophoretic light scattering, and the like). Suitable light scattering devices for determining particle size, polydispersity (i.e., calculating and displaying polydispersity values according to a Schultz-Zimm distribution), zeta-potential, and/or other parameters include, for example, a 90Plus particle analyzer including ZetaPlus zeta potential analysis software, Brookhaven Instruments Corporation, Holtsville, N.Y. Alternatively, a substantially equivalent system may be employed.

The transfection composition is preferably analyzed multiple times over the course of a particular time period at particular time increments (e.g., seconds, minutes, hours). Thus, for example, a measurement of the various properties of the transfection composition (e.g., effective average diameter, polydispersity, and/or zeta-potential) may be taken by a conventional light scattering device once every 0.5 minutes, 0.75 minutes, 1 minute, 1.25 minutes, 1.5 minutes, 1.75 minutes, or 2 minutes; these incremental measurements may be taken over the course of, for example, 5 minutes, 6 minutes, 7 minutes, 8 minutes, 9 minutes, 10 minutes, 11 minutes, 12 minutes, 13 minutes, 14 minutes, or minutes, or longer. In a particular embodiment, a measurement of the various properties of the transfection composition is taken by a light scattering device once every minute for 9 minutes. After several or even all of the desired measurements have been taken, a final value for one or more properties of the transfection composition may be determined using a mathematical extrapolation. Such calculations may be performed manually by one of skill in the art, or automatically by the light scattering device or other computing device.

Formation of the Transfection Compositions

In general, the transfection composition is formed by combining the above-described nucleic acid and polycationic composition comprising linear polyethyleneimine in an aqueous medium having a pH of at least 5.8 and incubating the combination. As noted above, the transfection composition may have an effective average diameter of about 425 to about 500 nm, about 480 to about 700 nm, or about 350 to about 850 nm, and a polydispersity about this average of less than 0.4.

Generally, the polycationic composition comprising linear polyethyleneimine and nucleic acid may be combined in the aqueous medium in any particular order. For example, the nucleic acid can be suspended in an aqueous medium lacking the polycationic composition and then the polycationic composition can be added to the nucleic acid suspension. Alternatively, the polycationic composition can be suspended in an aqueous medium lacking the nucleic acid and then the nucleic acid can be added to the polycationic composition suspension. In a preferred embodiment, the nucleic acid and the polycationic composition comprising linear polyethyleneimine are separately suspended in an aqueous composition and the separate suspensions combined to form an aqueous medium. In this embodiment, the polycationic composition suspension is preferably added to the nucleic acid suspension.

Regardless of the order of mixing, the combination is preferably agitated (e.g., by vortexing) to maximize the potential for interaction of the linear polyethyleneimine and nucleic acid.

The aqueous medium in which the nucleic acid and the polycationic composition comprising linear polyethyleneimine are combined preferably has a pH of at least 5.8. For example, the aqueous medium may have a pH of at least 6.0; at least 6.5; or at least 7.0. Preferably, the aqueous media has a pH of less than about 8.0. As noted above, the nucleic acid and the polycationic composition may be separately suspended in an aqueous composition, each separate aqueous composition having a pH of at least 5.8 (e.g., at least 6.0; at least 6.5; or at least 7.0), and the separate suspensions combined to form an aqueous medium. For example, the polycationic composition may be suspended in an aqueous composition having a pH of at least 5.8, and the nucleic acid may be suspended in an aqueous composition having a pH of at least 7.0, and the separate suspensions combined to form an aqueous medium having a pH of at least 5.8. In one embodiment, the aqueous medium has a pH of about 7.0 to about 7.6; more preferably in this embodiment the pH is about 7.1 to about 7.4.

In general, the combination of the nucleic acid and the polycationic composition comprising linear polyethyleneimine in an aqueous medium having a pH of at least 5.8 forms an aqueous transfection reagent which may be employed as described above to transfect the CHO cells (i.e., the aqueous transfection reagent containing the aqueous medium and the transfection composition is delivered to the CHO cells in culture). The pH of the aqueous transfection reagent generally depends on the pH of the aqueous compositions used in the combination of the nucleic acid and the polycationic composition comprising linear polyethyleneimine described above. In one embodiment, the aqueous transfection reagent has a pH of about 7.0 to about 7.6; more preferably in this embodiment the pH is about 7.1 to about 7.4.

The nucleic acid and the polycationic composition comprising linear polyethyleneimine are preferably combined in the presence of a pH buffer. For example, the aqueous composition(s) employed in the combination of the nucleic acid and the polycationic composition may contain a pH buffer. By way of further example, the nucleic acid and the polycationic composition comprising linear polyethyleneimine may be separately suspended in an aqueous composition, at least one of the separate suspensions comprising a pH buffer, and the separate suspensions combined. In a particular embodiment, the aqueous composition in which the polycationic composition and the nucleic acid are separately suspended and thereafter combined is a pH buffer. Any pH buffer encompassing the desired pH range for the aqueous medium can be used to combine the linear polyethyleneimine and the nucleic acid. Suitable pH buffers for use herein include appropriate concentrations of phosphate buffer or N-[2-hydroxyethyl]piperazine-N'-[2-ethanesulfonic acid] (HEPES buffer). For instance, the pH buffer may comprise from about 5 mM to about 30 mM HEPES buffer. Thus, for example, the pH buffer may comprise 10 mM, 15 mM, 20 mM, or 25 mM HEPES buffer. In a particular embodiment, the pH buffer comprises from about 10 mM to about 25 mM HEPES buffer; more preferably in this embodiment about 20 mM HEPES buffer.

It has been found that forming the transfection composition in an aqueous medium having a pH of at least 5.8 and/or in the presence of a pH buffer such as those described above provides improved transfection composition properties. For instance, it appears that forming the transfection composition in an aqueous solution having a pH of at least 5.8 and/or in the presence of a pH buffer assists in the formation of particles having a relatively low polydispersity (i.e., the population of particles are of a more uniform size, which can result in improved transfection efficiencies). Additionally, the use of an aqueous solution having a pH of at least 5.8 and/or a pH buffer tends to reduce the incidents of pH shift when the transfection composition is combined with the CHO cells, which can also improve transfection efficiency and/or polypeptide production by the transfected CHO cells.

The aqueous solution having a pH of at least 5.8 preferably includes a physiologically compatible ionic salt. In general, the aqueous medium having a pH of at least 5.8 includes about 100 to about 200 mM of a physiologically compatible ionic salt; thus, for example, the aqueous medium may contain about 125 to about 175 mM of a physiologically compatible ionic salt. In one embodiment, the aqueous medium having a pH of at least 5.8 includes about 150 mM of a physiologically compatible ionic salt. Suitable physiologically compatible ionic salts include, for instance, sodium chloride, potassium chloride, calcium chloride, magnesium chloride, and the like. In various embodiments, the aqueous solution comprises HEPES-buffered saline.

The amount of nucleic acid utilized in the formation of the transfection composition can depend on a variety of factors. Among such factors are the desired final nucleic acid concentration in the transfection composition at transfection (i.e., when the transfection composition is combined with the CHO cells in the aqueous medium), whether or not the density of the CHO cells is concentrated prior to transfection, and/or whether the aqueous media (e.g., conditioned media) is replaced with fresh aqueous medium before and/or after transfection. Typically, the nucleic acid concentration at transfection is from about 0.5 to about 3 µg/ml. In some instances, a nucleic acid concentration towards the higher end of this range is desirable. Thus, in one embodiment the final nucleic acid concentration at transfection is from about 2 to 3 µg/ml (e.g., 2.1, 2.3, 2.5, 2.7, or 2.9 µg/ml); more preferably in this embodiment about 2.5 µg/ml. In other instances, a nucleic acid towards the lower end of the above range (i.e., 0.5 to 3 µg/ml) is desirable. Thus, in another embodiment the final nucleic acid concentration is from about 0.5 to about 2.25 µg/ml; more preferably in this embodiment from about 0.5 to about 2 µg/ml. For example, the final nucleic acid concentration may be from about 0.8 to about 1.5 µg/ml, or from about 1.0 to about 2.0 µg/ml (e.g., 1.1, 1.3, 1.5, 1.7, or 1.9 µg/ml). In a particular embodiment, the final nucleic acid concentration at transfection is about 1.5 µg/ml.

The amount of linear polyethyleneimine utilized in the formation of the transfection composition generally depends on the desired ratio of amine moieties (N) to phosphate moieties (P) (i.e., N/P ratio) in the transfection composition and the desired effective average diameter and/or polydispersity of the transfection composition. The N/P ratio is a measure of the ionic balance between the nucleic acid and the linear polyethyleneimine. In general, varying the N/P ratio affects the effective average diameter of the transfection composition; that is, smaller N/P ratios tend to result in larger average particle diameters where larger N/P ratios result in smaller average particle diameters. To calculate the amount of linear polyethyleneimine to be combined with nucleic acid in order to obtain a desired N/P ratio, the following formula may be used:

linear polyethyleneimine (ml)=[(mg nucleic acid×3) (N/P)]/concentration of linear polyethyleneimine in nitrogen residues As previously noted, the particular linear polyethyleneimine formulation used in forming the transfection composition preferably has a known purity level and molecular weight in order to determine the concentration of linear polyethyleneimine in nitrogen residues. The transfection composition containing linear polyethyleneimine generally has an N/P ratio of about 15:1 to about 30:1. In one embodiment, the transfection composition containing linear polyethyleneimine (e.g., 25 kDa, 7-10% impure) has an N/P ratio of about 18:1 to about 28:1; more preferably in this embodiment the transfection composition has an N/P ratio of 23:1. It has been found that transfecting CHO cells with a transfection composition having an N/P ratio within the above ranges (e.g., about 15:1 to about 30:1) provides improved transfection efficiencies and/or polypeptide production.

Once the linear polyethyleneimine and nucleic acid have been combined, the combination is incubated. It is generally during this incubation period that the linear polyethyleneimine and nucleic acid interact as described above to form the transfection composition (i.e., the population of particles comprising nucleic acid and the polycationic composition comprising linear polyethyleneimine are formed). Varying the length of time that the nucleic acid and the polycationic composition comprising linear polyethyleneimine are incubated can also affect the effective average diameter of transfection composition; that is, longer incubation times generally tend to produce a population of particles having a larger effective average diameter. In general, the combination is incubated for at least 5 minutes. Typically, the combination is incubated for about 5 minutes to about 20 minutes. For example, the combination may be incubated for about 6 minutes to about 18 minutes, about 8 minutes to about 15 minutes, or from about 8 minutes to about 12 minutes. In a particular embodiment, the combination is incubated for about 10 minutes. Alternatively, it is contemplated that longer or shorter incubation times may be employed; longer incubation times, however, generally result in transfection compositions having larger than desired effective average diameters and/or polydispersities as noted above, while shorter incubation times tend to adversely affect transfection efficiency and/or level of polypeptide production.

The conditions during the incubation are not narrowly critical. Generally, the combination is incubated at room temperature (e.g., 20-27° C.). However, any incubation condition that combines with the other parameters described herein to produce the desired transfection efficiency and/or level of polypeptide production is contemplated for use in the processes of the present invention.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

Materials and Methods

Cell Culture

CHO-S cells (Gibco/Invitrogen, Carlsbad, Calif.), a subclone of the common CHO-K1 line that has been selected for suspension growth in serum-free media, were grown in Freestyle™ CD17 serum-free and human-, animal-, and plant-derived component-free media that was substantially free of anti-clumping agents and supplemented with 0.01% Pluronic® F68 (BASF, Mount Olive, N.J.) and antibiotics. Cells were cultured in sterile, disposable Erlenmeyer flasks (125, 500, or 2000 ml) using 20-30% of the nominal volume at 125-140 r.p.m. under standard humidified conditions (37° C. and 8% $CO_2$).

Vectors and Other Reagents

For optimization experiments, the pEGFP-C1 (Accession number U55763, Clontech, Mountain View, Calif.) plasmid or a plasmid pair comprising a plasmid encoding a hIgG heavy chain and a plasmid encoding a hIgG light chain were used, and relatively high purity, low endotoxin plasmids were prepared (Lamda Biotech, Inc., St. Louis, Mo.). 25 kDa linear polyethyleneimine (Polysciences, Inc., Warrington, Pa.) was dissolved in anhydrous absolute ethanol (EtOH) to make stock solutions of either 1 mg/ml (22.7 mM Nitrogen residues) or 100 mg/ml (2270 mM Nitrogen residues), sterilized by 0.22 μm filtration, and stored at 4° C.

Formation of the Transfection Composition

Calculated amounts of DNA were diluted in 1×HEPES-buffered saline pH 7.3 (HBS). Varying amounts of linear polyethyleneimine (LPEI) were used based on the desired N/P ratio. Linear polyethyleneimine was diluted in HBS in a total volume equal to the volume of diluted DNA. The LPEI dilution was immediately added to the DNA dilution. The complexes were vortexed and incubated at room temperature for 10 minutes. Calculation of N/P was based on the formula:

$$\text{Amount of } LPEI \text{ } (\mu g) = \frac{\text{Amount of } DNA \text{ } (\mu g) \times 3 \times N/P \text{ Ratio}}{mM \text{ nitrogen residues in } LPEI}$$

Calculations were based on a 100% pure linear polymer. Based on NMR analysis, the linear polyethyleneimine stock purity was ~90.5%.

Small-Scale Transient Transfections for High Transfection Efficiency

To obtain a high transfection efficiency of CHO cells expressing GFP, two days before transfection cells were seeded at 1.5-2×10$^5$ cells/ml in 50 ml Freestyle™ CD17 media in a 125 ml Erlenmeyer shake flask. On the day of transfection, 3×10$^7$ cells in early log phase (up to 1.5×10$^6$ cells/ml) were harvested and pelleted by centrifugation. Cells were resuspended at a concentrated cell density of 2×10$^6$ cells/ml in 15 ml pre-warmed media. Transfection compositions were made as described above using 2.5 μg/ml DNA diluted in 750 μl HBS. LPEI at an N/P of 23:1 was diluted in 750 μl HBS. 1.5 ml particles were then added to the concentrated cell culture. 4-6 hours later, the cells were diluted to 45 ml total volume with fresh pre-warmed media. For GFP expression, the cells were assayed at 48 hours post-transfection by flow cytometry.

Alternate Small-Scale Transient Transfections for Secreted Protein Production

To obtain a high accumulation of transiently expressed protein in culture, two days before transfection cells were seeded at 1.5-2×10$^5$ cells/ml in 45-50 ml Freestyle™ CD17 media in a 125 ml Erlenmeyer shake flask. On the day of transfection, 4.5×10$^7$ cells in early log phase (up to 1.5×10$^6$ cells/ml) were harvested and pelleted by centrifugation. Cells were resuspended at 1×10$^6$ cells/ml in 45 ml pre-warmed media. Transfection compositions were made as described above. 1.5 μg/ml DNA was diluted in 1350 μl HBS in a 15 ml sterile conical tube. LPEI at an N/P of 23:1 was diluted in 1350 μl HBS in a 15 ml sterile conical tube. 2.7 ml of particles were added to the cell culture. For scaling up, total volume of particles (ml) was calculated using the amount of DNA (mg) used for transfection multiplied by a factor of 40. DNA(s) were diluted in one half the total volume and LPEI was diluted in one half the total volume. If co-transfections were performed, molar ratios were optimized for each plasmid pair. For heavy and light chain monoclonal antibody transfection, the most common ratio used was 2:1 light chain:heavy chain. Cells were supplemented 48 hours post-transfection with 0.09% Pluronic® F68 (BASF, Mount Olive, N.J.) (for a total of 0.1%) and Anti-Clumping Agent (01-0057, Invitrogen, Carlsbad, Calif.) and were maintained for up to 9 days in culture until cell viabilities dropped below 50%. Antibody expression was quantified by ELISA using standard curve analysis.

Large-Scale Transient Transfections Using Diafiltration to Remove Cellular-Derived Solutes and Debris Two days prior to transfections, CHO cells were seeded at 1.5-2×10$^5$ cells/ml in approximately 6.0 liters of Freestyle™ CD17 media in a Celligen Plus 7.5 liter stirred tank bioreactor (New Brunswick Scientific Edison, N.J.). The bioreactor was run in suspension mode with a pitched blade impeller agitating at 15 rpm. The running parameters were set at 60% dissolved oxygen, pH 7.1 at a temperature of 37° C. Cells were cultured to early log phase growth and conditioned media was removed using continuous diafiltration with a 2800 cm$^2$ 0.2 μm microfiltration cross flow hollow fiber filter membrane (GE Healthcare Product No. CFP-2-E-6A, Piscataway, N.J.). Cells were resuspended in pre-warmed fresh media to 1×10$^6$ cells/ml and the total volume was transfected as described above. Antibody expression was quantified by ELISA using standard curve analysis.

ELISA Analysis

Sandwich ELISA's were performed using purified Anti-human IgG (Fc Specific) monoclonal antibody clone HP6043 (Leinco Technologies, Inc., St. Louis, Mo.) coating antigen and Goat anti-human IgG Fcγ HRPO detection antibody (Jackson ImmunoResearch Laboratories, Inc., West Grove, Pa.). Dilution series of samples and standards were done in duplicate and 3 points along the linear portion of the titration were averaged to calculate titer concentration. For each monoclonal antibody assayed, a specific purified protein standard was used to calculate the titer concentration.

Flow Cytometry

GFP was analyzed by flow cytometry using a FACscan with CellQuest 3.3 software (Becton Dickinson, Franklin Lakes, N.J.). Negative thresholds were set using untransfected cells for each independent experiment.

Transfection Composition Particle Sizing

Particle sizing was performed using a 90Plus Particle Size Analyzer with a He—Ne laser at 632 nm using ZetaPlus Particle Sizing Software Ver. 2.31 and PALS Zeta Potential Analyzer Ver. 3.16 (Brookhaven Instruments Corp., Holtsville, N.Y.). The machine was calibrated with 90 nm Nanosphere Size Standards (Duke Scientific Corp., Fremont, Calif.).

Example 1

Figure 1D:
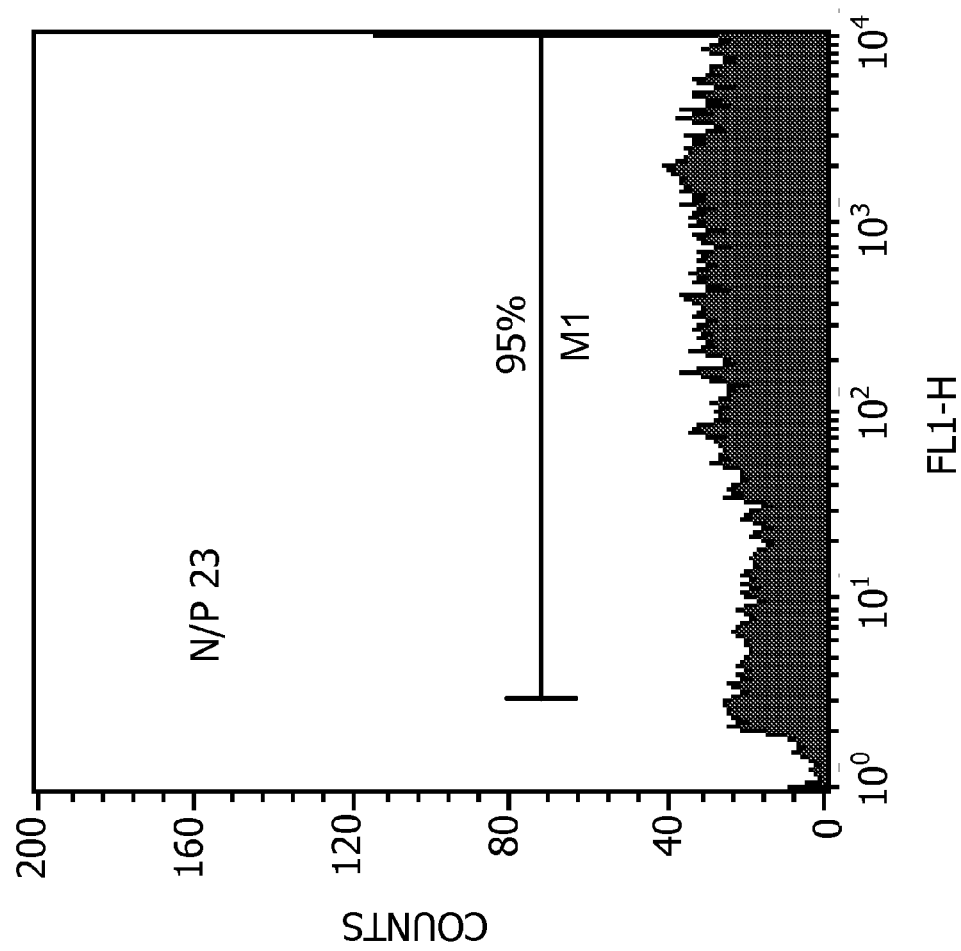
Figure 1F:
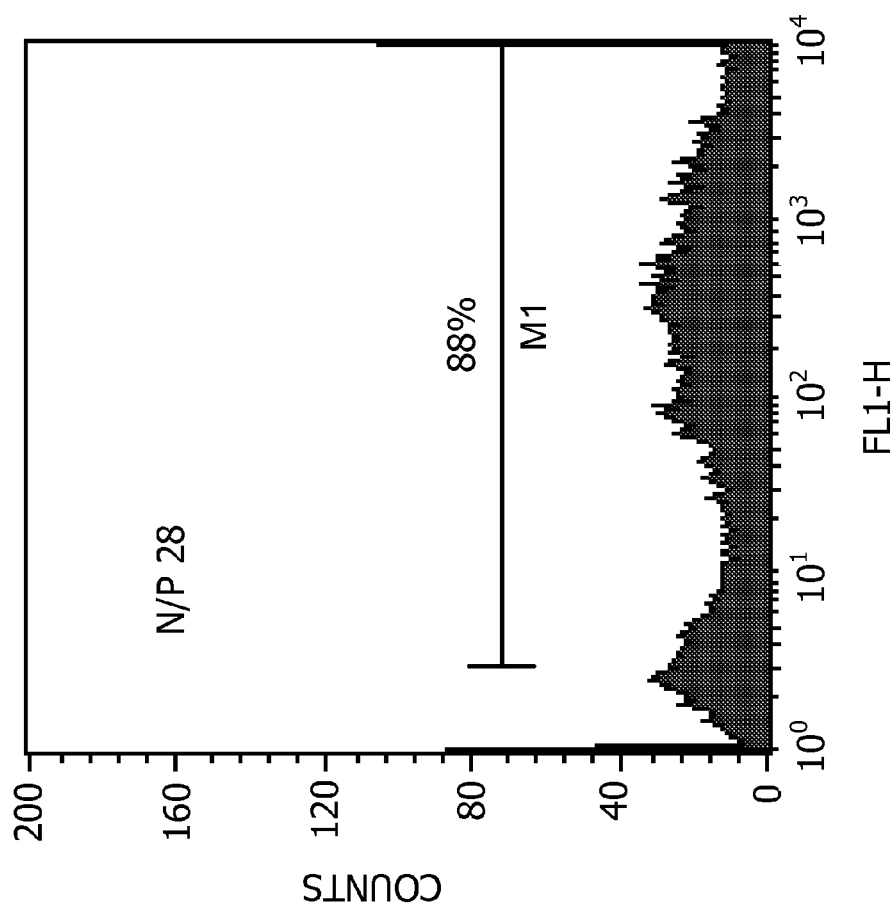

Under constant pH and incubation time, particle size is directly related to N/P ratio. Smaller N/P ratios result in larger average particle diameters where larger N/P ratios result in smaller average particle diameters. To determine the optimal particle size to transfect CHO-S cells, N/P ratios were varied and transfection efficiencies were determined by evaluating percent of GFP positive cells. CHO-S cells were effectively transfected as described above using a range of N/P ratios. See FIGS. 1A, 1B, 1C, 1D, 1E, and 1F. At high N/P ratios, some cytotoxity was observed. The optimal N/P ratio for CHO-S cells was observed to be 23:1. This N/P ratio gave the highest transfection efficiency (95%) and maintained cell viabilities greater than 90%. See FIG. 1D. With N/P ratios from 18:1 to 28:1, about 90% of the cells were transfected. See FIGS. 1B, 1C, 1D, and 1E. At lower N/P ratios of 15:1 or less, the percent of GFP positive cells decreased to 70% and less. See FIG. 1A. For all subsequent protein expression assays, an N/P ratio of 23:1 was used.

Example 2

Figure 2A:
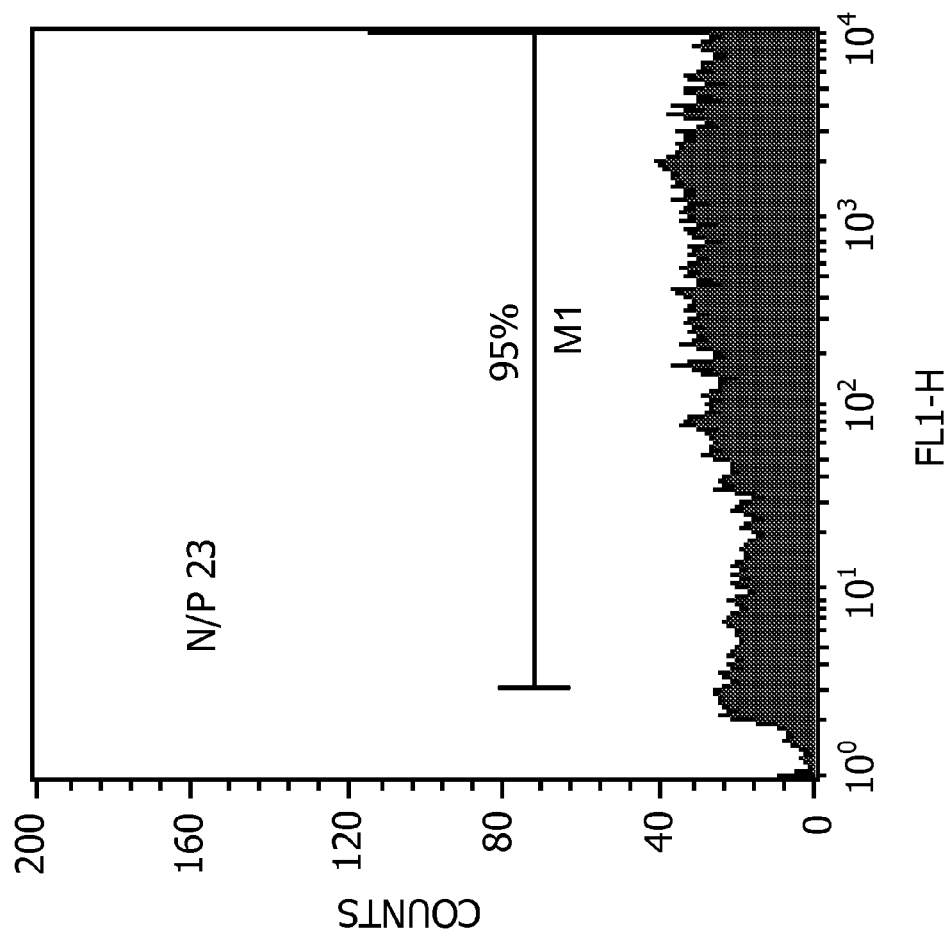
FIG. 2A is a flow cytometry histogram showing GFP expression of transfected CHO cells 48 hours after transfection with 2.5 µg/ml pEGFP-C1 and 25 kDa linear polyethyleneimine using particles formed in HEPES-buffered saline with a pH of 7.3 and with an N/P ratio of 23:1.
Figure 2B:
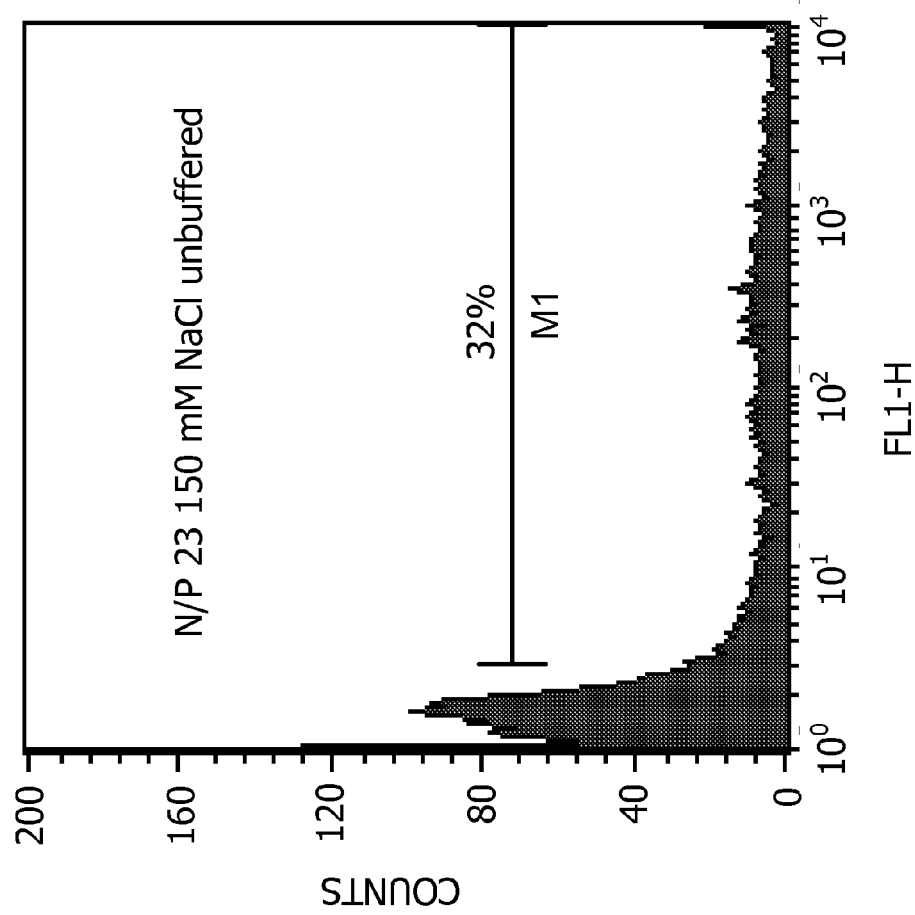
FIG. 2B is a flow cytometry histogram using the same protocol and conditions as in FIG. 2A, but in FIG. 2B the particles were formed in nonbuffered 150 mM NaCl, with an unadjusted pH. See Example 2.

Once an optimal N/P ratio was established, the effect of pH was analyzed. In an unbuffered system, i.e., when the particles are made in 150 mM NaCl (pH 5.8) versus the HEPES-buffered saline (150 mM NaCl) pH buffered at 7.3, the percent positive GFP expression decreased. As shown in FIG. 2A, forming the particles in a buffered system resulted in a 95% transfection efficiency, as compared to a 32% transfection efficiency in an unbuffered system (FIG. 2B).

Example 3

Figure 3B:
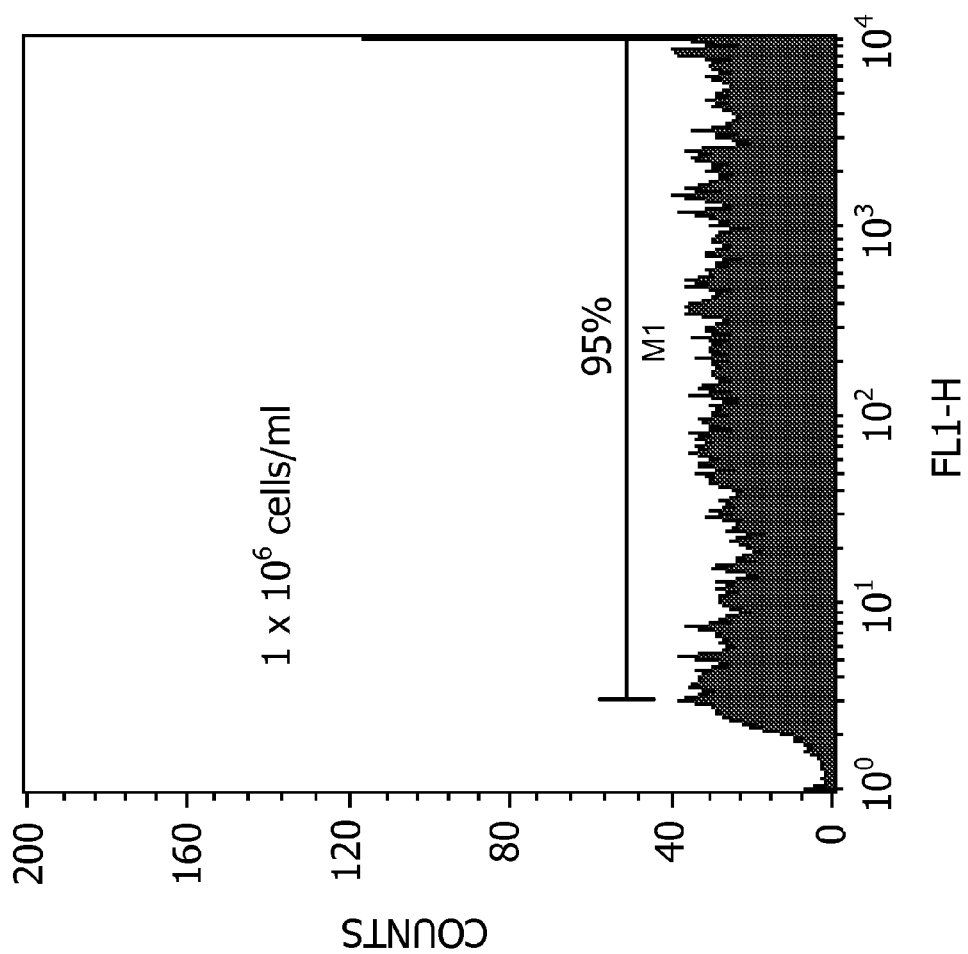
Figure 3D:
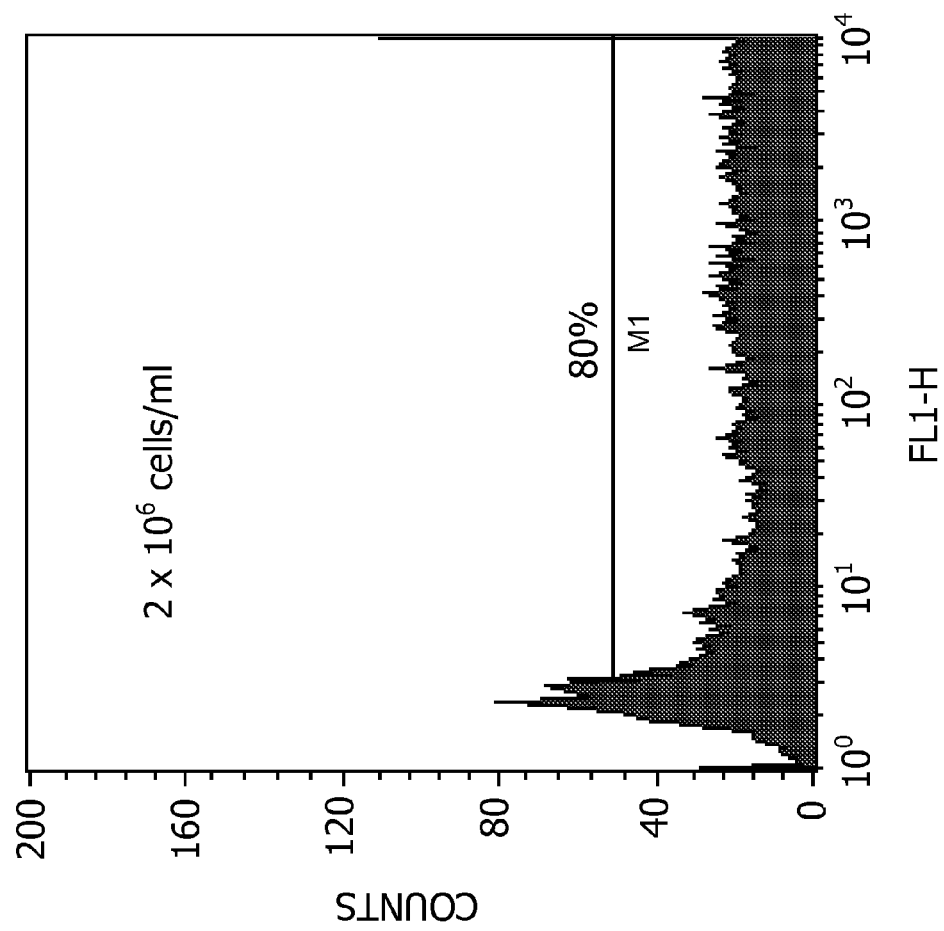
Figure 3E:
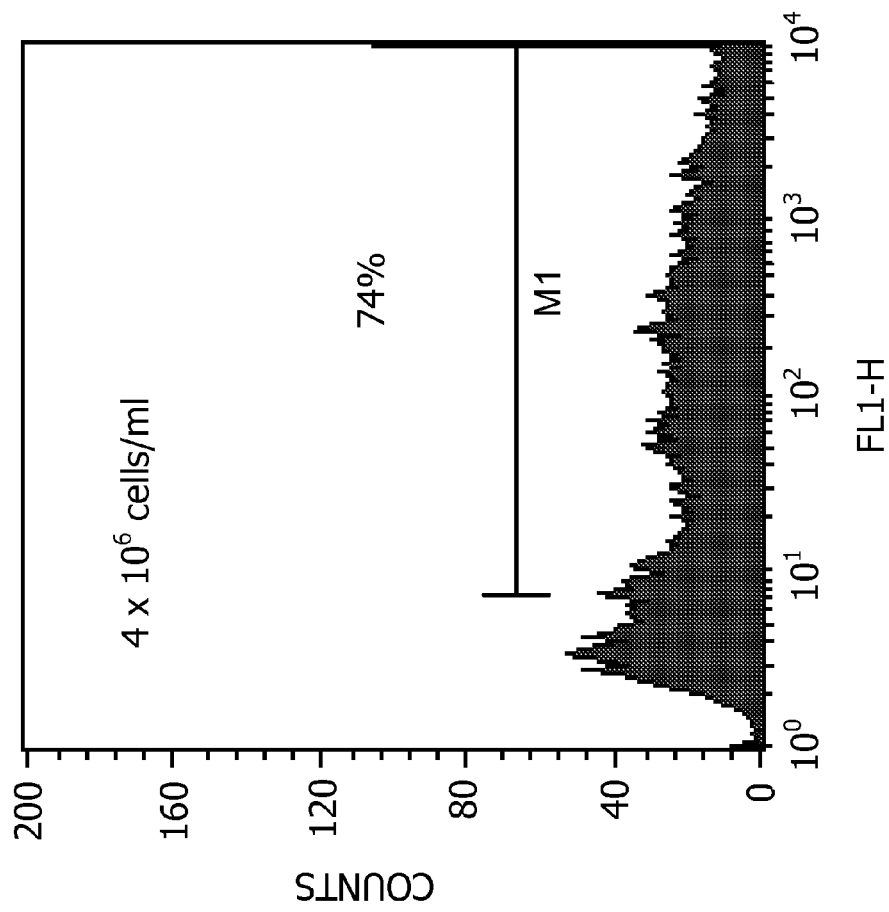

In addition to particle size and distribution, growth characteristics of the CHO-S cells were optimized to achieve the highest transfection efficiencies. At optimal conditions, CHO-S cells grew exponentially with a doubling time of <12 hours. When cells were harvested at the early stages of the exponential growth and concentrated to a higher density prior to transfection, the overall transfection efficiencies increased. In this example, early log phase was approximately $5 \times 10^5$ to $10 \times 10^5$ cells/ml when seeded at $1.5 \times 10^5$ cells/ml. When cells were allowed to grow to higher densities before transfection, a decrease in transfection efficiency was seen. The cells were concentrated prior to transfection from different densities ranging from $4 \times 10^5$ cells/ml to $4 \times 10^6$ cells/ml of the aqueous medium to a final concentration of $2 \times 10^6$ cells/ml of the aqueous medium. As shown in FIGS. 3D and 3E, transfection efficiency decreases when the cells are transfected later in the growth phase (i.e., out of the early log phase of growth), as compared to FIGS. 3A, 3B, and 3C showing relatively high transfection efficiencies for cells transfected in the early log phase of growth.

Example 4

Figure 4A:
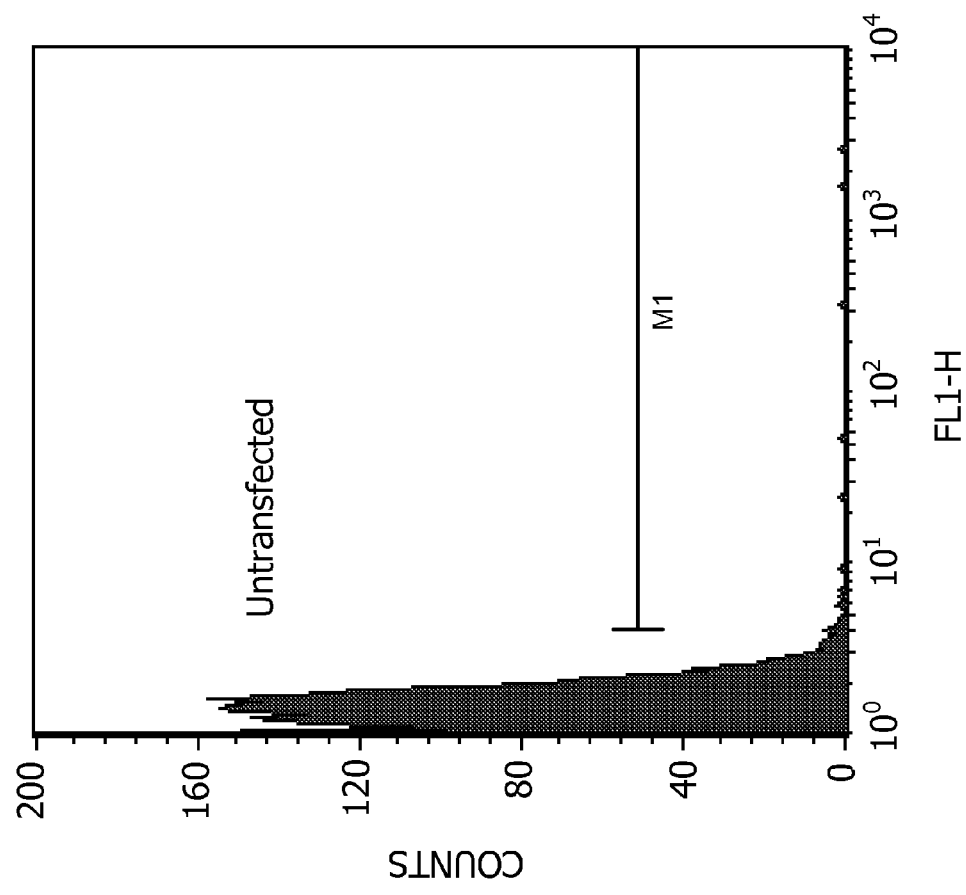
FIG. 4A is a flow cytometry histogram showing untransfected CHO cells showing no GFP expression.

Resuspending cells in fresh growth media prior to transfecting was also shown to improve transfection efficiency. This was accomplished by either centrifugation and resuspension or diafiltration. FIGS. 4B and 4C show a representative experiment where cells were transfected in fresh media (FIG. 4B) versus conditioned media (FIG. 4C). In both cases, $3 \times 10^7$ cells were seeded 48 hours prior to transfection, grown to $8 \times 10^5$ cells/ml, and centrifuged. Cell pellets were resuspended in either pre-warmed fresh media or their own conditioned media. Flasks were transfected using the particles formed as above and assayed 48 hours post transfection for GFP expression. As shown in FIGS. 4B and 4C, approximately 24% reduction in the number of GFP positive cells were seen in the flask transfected with conditioned media. Control untransfected cells are shown in FIG. 4A.

Example 5

In this example, a system for rapid, high yield production of monoclonal antibodies was tested by performing a small scale transfection using plasmids encoding the light and heavy chain of a human IgG antibody. The transfection was done using molar ratios of the 2 plasmids for a total of 2.5 µg/ml DNA. Transfection procedure was identical to the GFP transfections described above. 48 hours post-transfection, additional 0.09% Pluronic® F68 (BASF, Mount Olive, N.J.) and Anti-Clumping Agent (01-0057, Invitrogen, Carlsbad, Calif.) were added to the cultures to prolong growth. Supernatant were harvested at different time points and assayed for total hIgG concentration.

Figure 5:
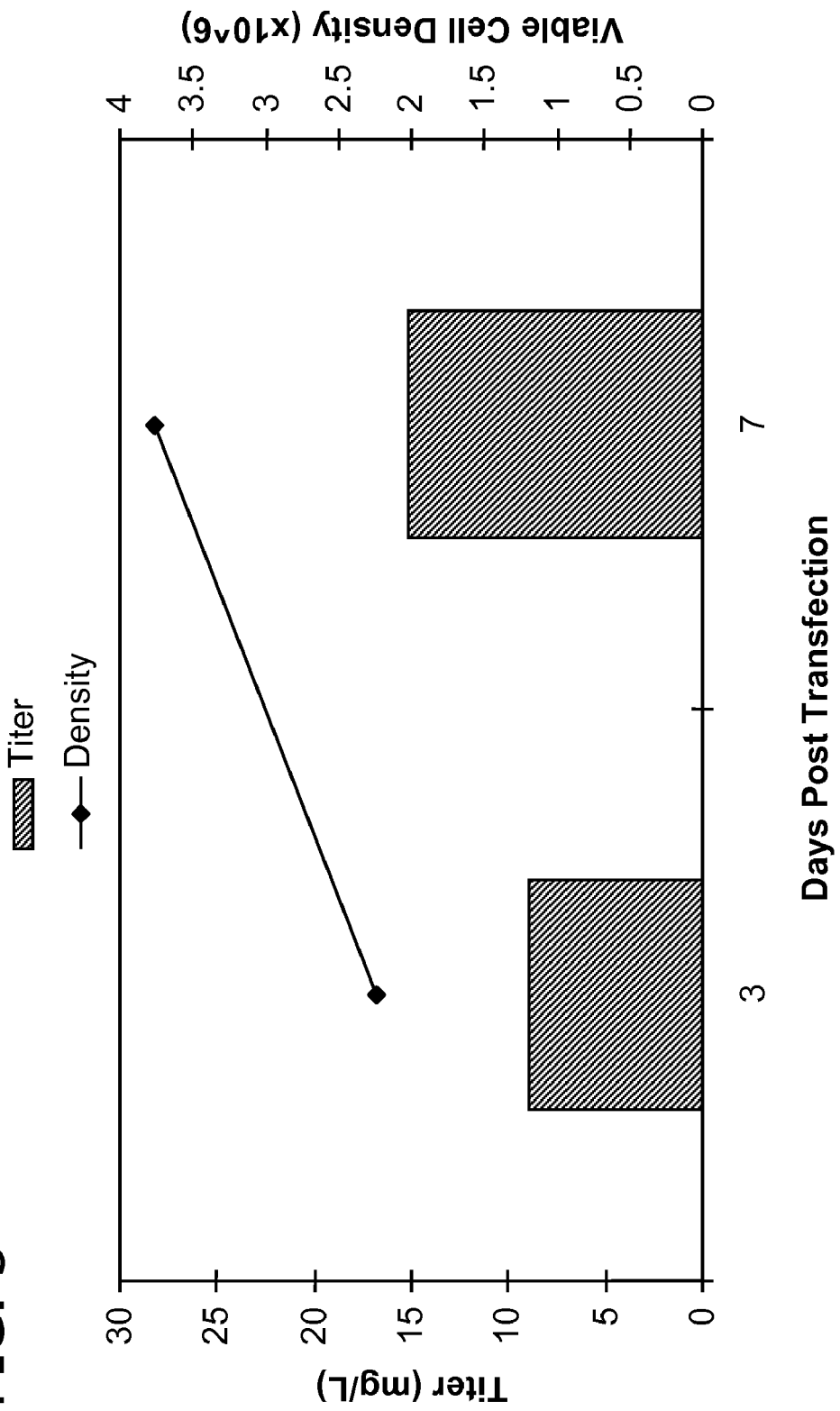
FIG. 5 is graph of the titer from a 45 milliliter small-scale human monoclonal antibody production run. Viable cell densities were calculated using trypan blue exclusion and manual counting with a hemocytometer. The titers were calculated from ELISA standard curve analysis. Titer data from day 3 and day 7 post-transfection are shown. Seven days after transfection, the average yield was about 15 mg/L. See Example 5.

FIG. 5 shows a representative production run where after 7 days post-transfection, the average yield was 15.09 mg/L.

Example 6

Two days prior to transfection, CHO-S cells were seeded in a 7.5 L stirred tank bioreactor at a density of $1.5 \times 10^5$ cells/ml and allowed to reach a density of $7.9 \times 10^6$ cells/ml with a viability of 100%. Using cross flow microfiltration, the cells were concentrated to a density of $2.1 \times 10^6$ cells/ml with a final transfection volume of 2.0 L. Approximately 95% of the conditioned media in the bioreactor was replaced with fresh pre-warmed Freestyle™ CD17 protein free media using continuous diafiltration with a cross flow hollow fiber filter membrane maintaining a constant cell density and transfection volume. Six liters of fresh pre-warmed Freestyle™ CD17 media was pumped into the bioreactor while removing conditioned media using continuous diafiltration at the same rate to maintain the cell density and transfection volume.

Figure 6B:
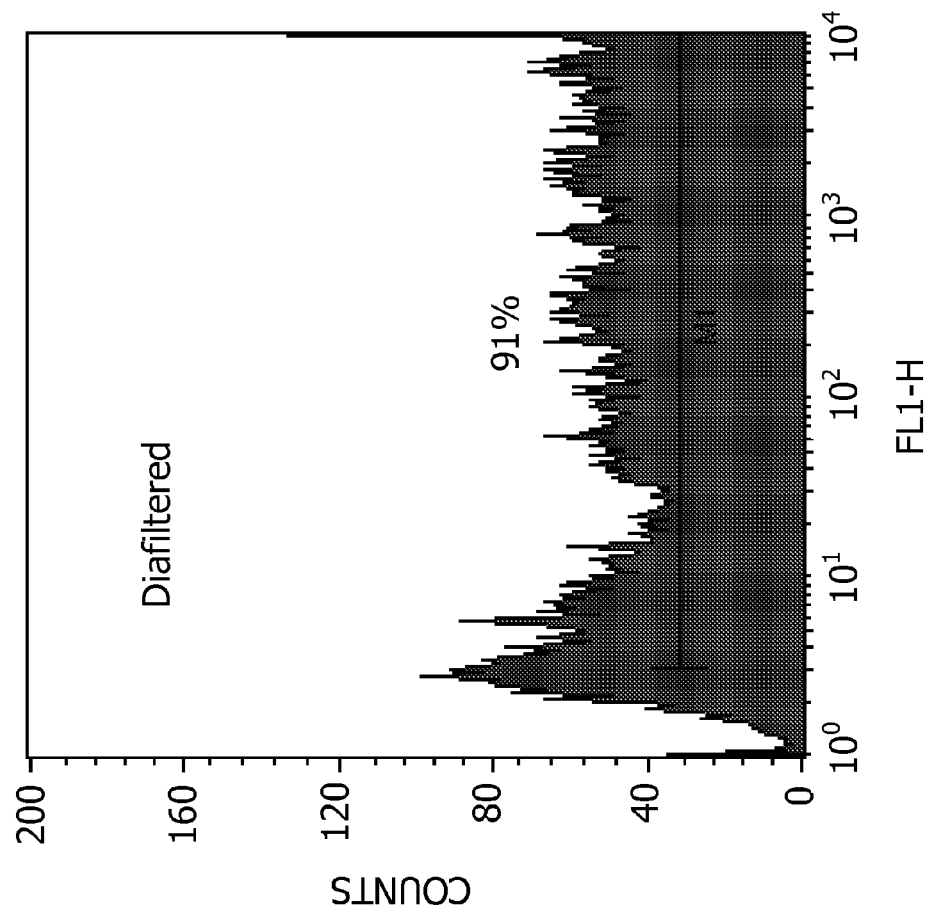
FIG. 6B is a flow cytometry histogram showing GFP expression of transfected CHO cells 48 hours after transfection with 2.5 µg/ml pEGFP-C1 and 25 kDa linear polyethyleneimine using particles formed in HEPES-buffered saline with a pH of 7.3 and an N/P ratio of 23:1. During culture and prior to transfection, conditioned media was removed from the bioreactor and replaced with pre-warmed fresh media using continuous diafiltration. See Example 6. Transfection efficiency (as measured by GFP expression) of CHO cells transfected using a continuous diafiltration protocol was similar to the transfection protocol in which conditioned media was replaced with fresh media prior to transfection. Compare Example 6 and FIG. 6B and Example 4 and FIGS. 4B and 4C.

Cells were transfected at a density of $2.1 \times 10^6$ cells/ml with a mammalian expression vector encoded with green fluorescent protein (GFP) as described above and analyzed approximately 48 hours latter for GFP expression by flow cytometry. As shown in FIG. 6B, 91% transfection efficiency was achieved, compared to an untransfected control population (FIG. 6A).

Example 7

In this example, cells were seeded at a low density and allowed to grow to $1 \times 10^6$ cells/ml (early log phase), at which point they were harvested and centrifuged to remove conditioned media. Instead of transfecting the cells at a concentrated volume of $2 \times 10^6$ cells/ml, cells were resuspended at $1 \times 10^6$ cells/ml in the total volume for the transfection. The particles were made in a volume 1/30th the total volume using 0.833 µg/ml total DNA and LPEI at an N/P of 23:1. Cells were transfected and allowed to grow undisturbed with no other media additions or changes. 48 hours post-transfection, additional 0.09% Pluronic® F68 (BASF, Mount Olive, N.J.) and Anti-Clumping Agent (01-0057, Invitrogen, Carlsbad, Calif.) were added to the cultures to prolong growth. Supernatant were harvested at different time points and assayed for total hIgG concentration. FIG. 7 shows two different experiments comparing the concentration and dilution protocol (as in Example 5) and the non-concentration and non-dilution protocol. On average a 10-25% increase in overall titer concentration using the non-dilution method was observed.

Example 8

In this example, nucleic acid concentration was evaluated using the alternate small-scale transfection protocol described above for secreted protein production. Cells were transfected as described in Example 7 and particles were made with varying amounts of DNA (0.833 µg/ml, 1.25 µg/ml, and 1.5 µg/ml). The particle volume was proportional to the amount of DNA added (i.e., for every 1 µg of DNA, 40 µl of particles were made). Amounts of LPEI were calculated using an N/P of 23:1. Cells were transfected and allowed to grow undisturbed with no other media additions or changes. 48 hours post-transfection, additional 0.09% Pluronic® F68 (BASF, Mount Olive, N.J.) and Anti-Clumping Agent (01-0057, Invitrogen, Carlsbad, Calif.) were added to the cultures to prolong growth. Supernatant were harvested at different time points and assayed for total hIgG concentration. FIG. 8 shows titer concentrations 5 days post-transfection of cells transfected with the varying amounts of DNA noted above. No significant improvements were seen above 1.5 μg/ml and at 2.5 μg/ml noticeable cell death was observed causing an overall decrease in the final titer.

What is claimed is:

1. A composition for transfecting Chinese hamster ovary (CHO) cells, the transfection composition containing a population of particles comprising linear polyethyleneimine and nucleic acid, the population having an average particle size and a polydispersity with the polydispersity being between 0 and 0.4, and the ratio of polyethyleneimine nitrogen moieties (N) to nucleic acid phosphate moieties (P) in the particles being 15:1 to 30:1 (N/P).

2. The composition as set forth in claim 1 wherein the population has an average particle size of from about 300 to about 900 nm.

3. The composition as set forth in claim 1 wherein the polydispersity of the population is less than 0.3.

4. The composition as set forth in claim 1 wherein the linear polyethyleneimine has a molecular weight of about 25 kDa.

5. The composition as set forth in claim 1 wherein the ratio of polyethyleneimine nitrogen moieties (N) to phosphate moieties (P) in the particles is 23:1 (N/P).

* * * * *